US007160272B1

(12) United States Patent  
Eyal et al.

(10) Patent No.: US 7,160,272 B1
(45) Date of Patent: Jan. 9, 2007

(54) Y-SITE MEDICAL VALVE

(75) Inventors: Ronen Eyal, Getta (IL); Claude A. Vidal, Santa Barbara, CA (US); Russell A. Redmond, Goleta, CA (US); David A. Chandos, North Richland Hills, TX (US)

(73) Assignee: Elcam Plastic, M.P. Merom Hagalil (IL)

( * ) Notice: Subject to any disclaimer, the term of this patent is extended or adjusted under 35 U.S.C. 154(b) by 352 days.

(21) Appl. No.: 10/453,677

(22) Filed: Jun. 2, 2003

Related U.S. Application Data

(60) Provisional application No. 60/385,167, filed on May 31, 2002.

(51) Int. Cl.
*A61M 5/00* (2006.01)
(52) U.S. Cl. ........................ 604/249; 604/246
(58) Field of Classification Search ............... 604/246, 604/249, 256
See application file for complete search history.

(56) References Cited

U.S. PATENT DOCUMENTS

| 3,566,874 A | 3/1971 | Shepherd et al. |
|---|---|---|
| 3,782,382 A | 1/1974 | Naftulin et al. |
| 3,889,710 A | 6/1975 | Brost |
| 3,954,121 A | 5/1976 | Kardos |
| 4,031,891 A | 6/1977 | Jess |
| 4,063,555 A | 12/1977 | Ulinder |
| 4,141,379 A | 2/1979 | Manske |
| 4,222,407 A | 9/1980 | Ruschke et al. |
| 4,236,517 A | 12/1980 | Langston et al. |
| 4,333,457 A | 6/1982 | Margulies |
| 4,369,812 A | 1/1983 | Paradis et al. |
| 4,387,879 A | 6/1983 | Tauschinski |
| 4,447,230 A | 5/1984 | Gula et al. |
| 4,460,367 A | 7/1984 | Wong et al. |
| 4,483,287 A | 11/1984 | Monigold et al. |
| 4,512,764 A | 4/1985 | Wunsch |
| 4,515,593 A | 5/1985 | Norton |
| 4,526,140 A | 7/1985 | Monigold et al. |
| 4,529,398 A | 7/1985 | Wong et al. |
| 4,556,086 A | 12/1985 | Raines |
| 4,559,036 A | 12/1985 | Wunsch |
| 4,581,028 A | 4/1986 | Fox, Jr. et al. |
| 4,592,920 A | 6/1986 | Murtfeldt |
| 4,601,880 A | 7/1986 | Wong et al. |

(Continued)

FOREIGN PATENT DOCUMENTS

WO        WO 94/22522        10/1994

OTHER PUBLICATIONS http://www.macc.cc.mo.us/~biology/Phys_Chem_Control.html, Mar. 26, 2002.

(Continued)

*Primary Examiner*—Sharon Kennedy
(74) *Attorney, Agent, or Firm*—Hoffman, Wasson & Gitler, P.C.

(57) ABSTRACT

A medical valve includes a valve body having a central fluid passageway defined therein. A movable piston adapted in size and shape to be located within said central fluid passageway of said valve body. A sealing interface is defined between said movable piston and said central fluid passageway. An upper seal is located at an upper portion of said sealing interface. It is formed by a seal carried by said valve body. A lower seal is located at a lower portion of said sealing interface, and is formed by a seal carried by said movable piston. The lower seal remains intact until after said upper seal is broken.

5 Claims, 32 Drawing Sheets

U.S. PATENT DOCUMENTS

| | | | |
|---|---|---|---|
| 4,603,152 A | 7/1986 | Laurin et al. | |
| 4,610,665 A | 9/1986 | Matsumoto et al. | |
| 4,626,245 A | 12/1986 | Weinstein | |
| 4,673,393 A | 6/1987 | Suzuki et al. | |
| 4,677,143 A | 6/1987 | Laurin et al. | |
| 4,708,870 A | 11/1987 | Pardini | |
| 4,758,609 A | 7/1988 | Rei et al. | |
| 4,768,518 A | 9/1988 | Peltonen | |
| 4,795,441 A | 1/1989 | Bhatt | |
| 4,915,688 A | 4/1990 | Bischof et al. | |
| 4,922,954 A | 5/1990 | Blomquist et al. | |
| 4,933,178 A | 6/1990 | Capelli | |
| 4,946,448 A | 8/1990 | Richmond | |
| 4,988,062 A | 1/1991 | London | |
| 5,019,096 A | 5/1991 | Fox, Jr. et al. | |
| 5,020,562 A | 6/1991 | Richmond et al. | |
| 5,049,140 A | 9/1991 | Brenner et al. | |
| 5,057,084 A | 10/1991 | Ensminger et al. | |
| 5,074,334 A * | 12/1991 | Onodera | 137/625.41 |
| 5,092,842 A | 3/1992 | Bechtold et al. | |
| 5,188,591 A * | 2/1993 | Dorsey, III | 604/33 |
| 5,190,525 A | 3/1993 | Oswald et al. | |
| 5,205,834 A | 4/1993 | Moorehead et al. | |
| 5,288,290 A * | 2/1994 | Brody | 604/32 |
| 5,308,322 A | 5/1994 | Tennican et al. | |
| 5,336,192 A | 8/1994 | Palestrant | |
| 5,353,837 A * | 10/1994 | Faust | 137/614.18 |
| 5,356,375 A | 10/1994 | Higley | |
| 5,429,485 A | 7/1995 | Dodge | |
| 5,431,185 A | 7/1995 | Shannon et al. | |
| 5,439,451 A * | 8/1995 | Collinson et al. | 604/247 |
| 5,535,771 A * | 7/1996 | Purdy et al. | 137/15.01 |
| 5,549,651 A | 8/1996 | Lynn | |
| 5,554,373 A | 9/1996 | Seabrook et al. | |
| 5,567,495 A | 10/1996 | Modak et al. | |
| 5,618,268 A | 4/1997 | Raines et al. | |
| 5,676,346 A * | 10/1997 | Leinsing | 251/149.1 |
| 5,681,468 A | 10/1997 | Sawan et al. | |
| 5,697,904 A | 12/1997 | Raines et al. | |
| 5,707,366 A | 1/1998 | Solomon et al. | |
| 5,738,662 A | 4/1998 | Shannon et al. | |
| 5,744,151 A | 4/1998 | Capelli | |
| 5,788,215 A | 8/1998 | Ryan | |
| 5,806,551 A * | 9/1998 | Meloul et al. | 137/1 |
| 5,817,325 A | 10/1998 | Sawan et al. | |
| 5,848,995 A | 12/1998 | Walder | |
| 5,849,311 A | 12/1998 | Sawan et al. | |
| 5,873,731 A | 2/1999 | Prendergast | |
| 5,873,904 A | 2/1999 | Ragheb et al. | |
| 5,877,243 A | 3/1999 | Sarangapani | |
| 6,009,902 A * | 1/2000 | Troiani et al. | 137/614.19 |
| 6,099,511 A * | 8/2000 | Devos et al. | 604/246 |
| 6,117,114 A * | 9/2000 | Paradis | 604/246 |
| 6,171,287 B1 * | 1/2001 | Lynn et al. | 604/249 |
| 6,224,579 B1 | 5/2001 | Modak et al. | |
| 6,227,413 B1 | 5/2001 | Bommer | |
| 6,245,048 B1 * | 6/2001 | Fangrow et al. | 604/249 |
| 6,261,271 B1 | 7/2001 | Solomon et al. | |
| 6,273,875 B1 | 8/2001 | Siman et al. | |
| RE37,357 E | 9/2001 | Lynn | |
| 6,344,035 B1 | 2/2002 | Chudzik et al. | |
| 6,364,861 B1 | 4/2002 | Feith et al. | |
| 6,482,188 B1 * | 11/2002 | Rogers et al. | 604/249 |
| 6,575,187 B1 * | 6/2003 | Leys et al. | 137/15.21 |
| 6,971,999 B1 | 12/2005 | Py et al. | |
| 6,991,215 B1 * | 1/2006 | Kiehne | 251/149.6 |
| 2002/0133124 A1 | 9/2002 | Leinsing et al. | |
| 2002/0147431 A1 * | 10/2002 | Lopez et al. | 604/256 |

OTHER PUBLICATIONS http://encarta.msn.com/find/Concise.asp?ti=06750000, Mar. 26, 2002.
http://www.bact.wisc.edu/microtextbook/ControlGrowth/sterilization.html, Mar. 26, 2002.
http://www.silverinstitute.org/news/prhealth.htm, Mar. 26, 2002.
http://www.aidsinfobbs.org/library/cdcsums/1993/012, Mar. 26, 2002.
http://www.panasonic.com.sg/consumer/index.cfm?type=products&product_id=56, Mar. 26, 2002.
http://www.edc.gov/drugresistance/miscellaneous/glossary.htm, Mar. 26, 2002.
Po-Ren Hsueh, et al., "Antimicrobial Drug Resistance in Pathogens Causing Nosocomial Infections at a University Hospital in Taiwan, 1981-1999", Emerging Infection Diseases, vol. 8, No. 1, Jan. 2002.
http://www.cidasal.es/mic_in.htm, Mar. 26, 2002.
Michael J. Richards, et al., "Nosocomical Infections in Pediatric Intensive care Units in the United States", Pediatrics, vol. 103, No. 4, Apr. 1999.
http://www.cdc.gov/ncidod/hip/NNIS@nnis.htm, Mar. 26, 2002.
http://www.cdc.gov/ncidod/eid/vol7no2/wenzelG4.htm, Mar. 26, 2002.
http://www.cdc.gov/ncidod/eid/vol7no2/mermel.htm, Mar. 26, 2002.
http://www.cdc.gov/niosh/hcwapp8.html, Mar. 26, 2002.
U.S. Appl. No. 60/385,167.

* cited by examiner

Y-SITE MEDICAL VALVE

CLAIM OF PRIORITY

1. This application claims the benefit of U.S. Provisional Patent Application Ser. No. 60/385,167, filed 31 May 2002, entitled "Improved Y-Site Medical Valve." This provisional application is incorporated herein as if fully set forth.

BACKGROUND OF THE INVENTION

1. Field of the Invention

This invention pertains to a novel way of creating an anti-bacterial barrier at the female opening of a needleless valve when it is in its closed condition.

2. Description of the Prior Art

When a medical valve is in a closed condition, it is essential that bacteria be prevented from entering it. The most likely area of entry for bacteria resides at the interface between the movable piston which constitutes the moving element of the valve mechanism and the entry to the female luer portion of the body, which constitutes the static portion of the valve.

Prior art designs have provided for an elastomeric seal attached to, or integral with, the movable piston. As the piston is urged toward the inside of the valve body by the luer tip of a syringe or IV connector, this seal acts as a wiper seal against the inside surface of the female luer in the body. An exemplary prior art valve system is depicted in FIG. 1. It includes movable wiper seal 13 and return spring 15.

This wiper seal is effective in preventing bacterial contamination; however, it presents two problems. Both of the problems are associated with the fact that the wiper seal must remain in contact with the inside surface of the female luer taper of the body throughout its downward travel as the valve opens:

1. Since the inside diameter of the taper becomes smaller and smaller as the wiper seal travels downward, the frictional force on the wiper seal and therefore on the valve piston keeps increasing. This means that the return spring (which causes the piston to move back to its original position when the syringe or IV connector is disengaged from the valve) must be strong enough to overcome this resistance. This is undesirable because this increased spring resistance will be brought to bear against the male luer tip while the syringe or IV connector is attached to the valve and, unless these devices have a luer lock feature (which many IV connectors do not), it increases the risk of accidental disconnection (with its associated clinical problem of depriving the patient of a needed fluid and/or medication).

2. As the male luer pushes the top of the piston downward, it is desirable that fluid injection be possible as soon as possible and regardless of where the distal tip of the luer ends up stopping. If the inside surface of the female luer of the body were perfectly smooth, the wiper seal would prevent any fluid flow into the valve. In order to prevent this condition, the inside surface of the female luer is generally grooved. If the wiper seal remains in contact with this grooved surface for an extended period of time, the elastomer can take a set, assume a dimpled configuration and, at least temporarily, provide a less effective bacterial seal when the valve is allowed to close again.

SUMMARY OF THE INVENTION

Generally, the general theme for these inventions is that they pertain to valve mechanisms with static seals, attached or integrally molded to the body of the valve, to perform a function otherwise performed by moving seals attached to the piston.

The above as well as additional objectives, features, and advantages will become apparent in the following description and associated drawings.

BRIEF DESCRIPTION OF THE DRAWINGS

The novel features believed characteristic of the invention are set forth in the appended claims. The invention itself however, as well as a preferred mode of use, further objectives and advantages thereof, will best be understood by reference to the following detailed description of the preferred embodiment when read in conjunction with the accompanying drawings, wherein:

DETAILED DESCRIPTION OF THE INVENTION

One concept of the present invention is to attach a static elastomeric circular seal to the top inside surface of the female luer in the valve body. The piston head can now be completely rigid. As soon as the piston head is depressed downward by a male luer, it disengages from the antibacterial static seal. This presents the following advantages:

1. The increased resistance problem mentioned in the case of a moving wiper seal disappears and, correspondingly, the return spring can be made lighter, thereby reducing the risk of accidental disconnection.

2. The tapered male luer experiences an increased interference with the static elastomeric seal as it penetrates inside the valve. This frictional force further reduces the risk of accidental disconnection.

3. Because the static seal contacts smooth surfaces at all times (the piston head when the valve is closed and the male luer when it is open) there is no risk of permanently or temporarily assuming a dimpled shape and thereby losing some of its effectiveness as an antibacterial barrier.

This principle can be used in a variety of valve configurations (such as, without limitation, in-line valves, Y valves, etc.) and with a variety of valve mechanisms.

The following text and associated drawings illustrate several possible configurations of the present invention.

Figure 1:
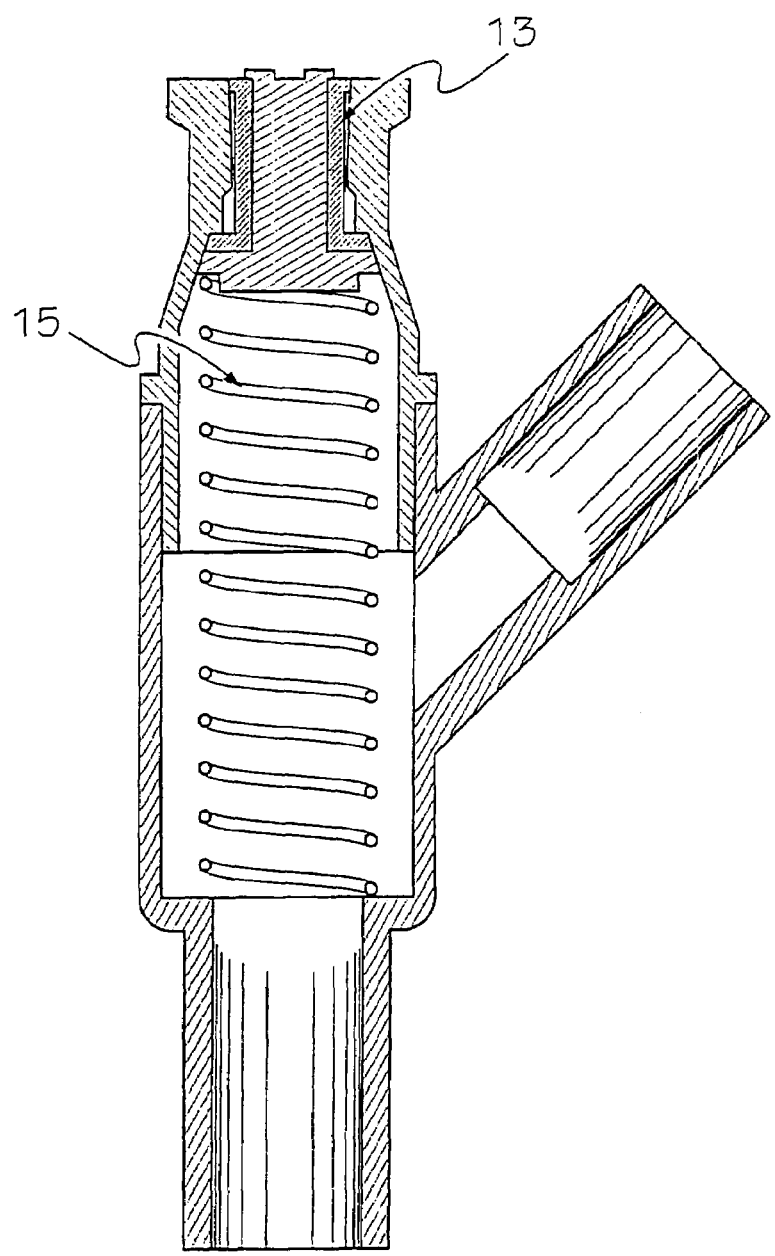
FIG. 1 is a simplified cross-section view of a prior art medical valve.
Figure 2:
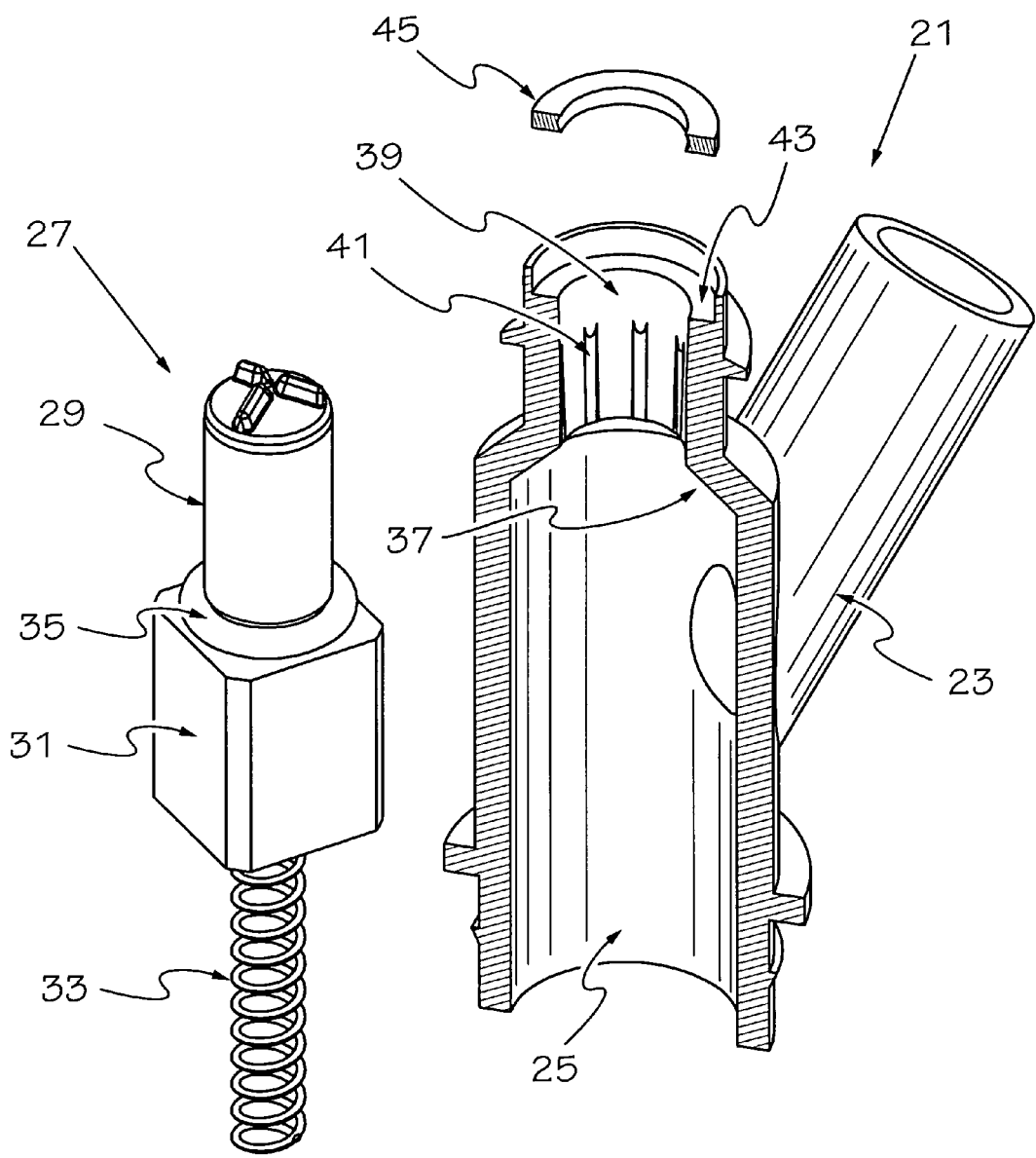
FIGS. 2 and 3 depict in exploded and fragmentary longitudinal views one embodiment of the present invention.

FIG. 2 is perspective view of the valve in a disassembled, or exploded, and partial fragmentary form. In FIG. 2, valve body 21 includes a y-branch, making it a y-site valve. A central cavity 25 is defined therein. It is adapted in size and shape to carry piston 27. Piston 27 includes a radially-reduced upper end 29 and a radially enlarged lower end 31. It includes a tapered shoulder at the transition between he two portions. Piston 27 is biased upward by spring 33. A seal, such as O-ring 35, is carried at the top of radially enlarged portion 31, and it is adapted to mate with shoulder 37 of central cavity 25.

Female luer 39 is carried at the top of valve body 21. It includes grooves 41 to allow fluid to pass into the central cavity when the luer valve is opened. A seal cavity 43 is formed in the upper portion of valve body 2. It is adapted to receive a seal such as O-ring seal 45.

Figure 3:
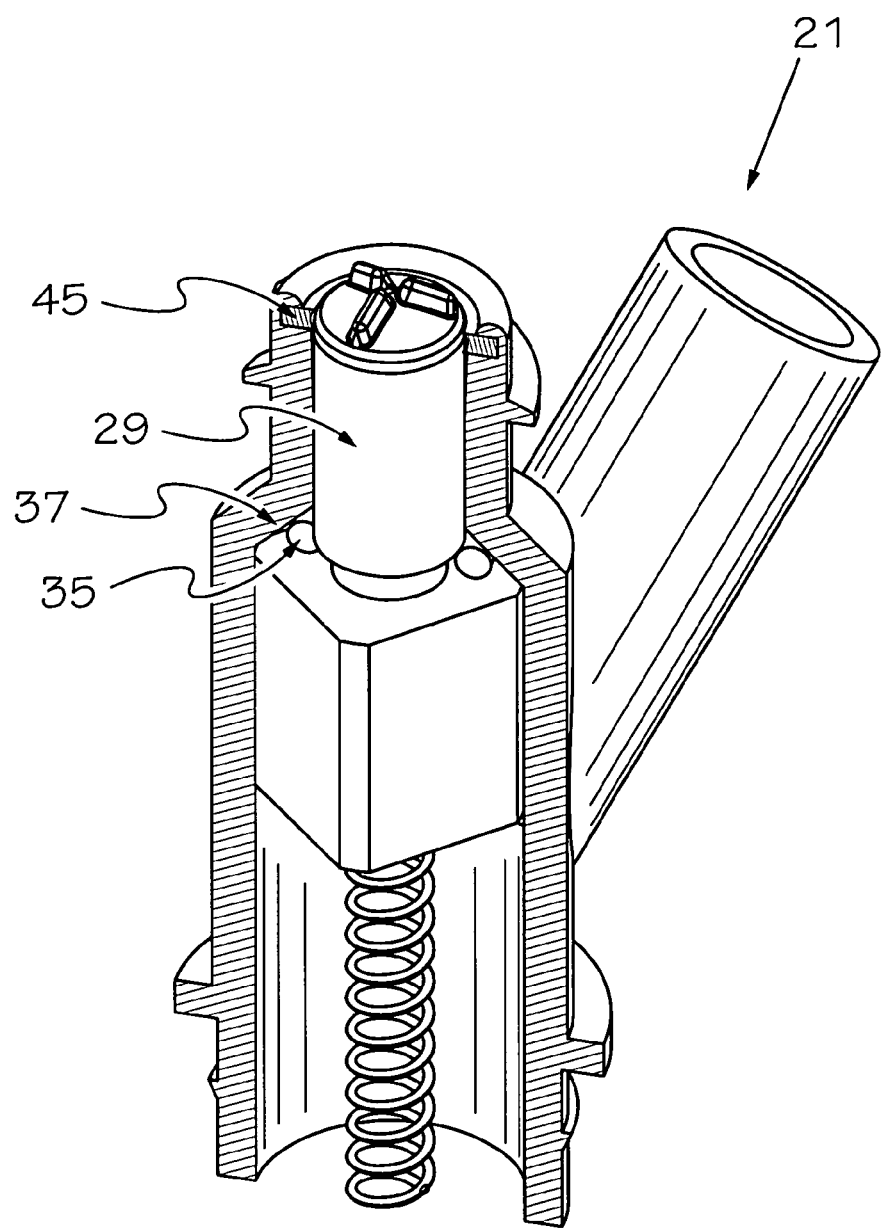

In accordance with this embodiment, two different seals are provided: (1) the seal between seal 35 and shoulder 37, and (2) the seal between seal 45 and the radially reduced upper end 29. FIG. 3 depicts the valve in a closed condition.

Figure 4:
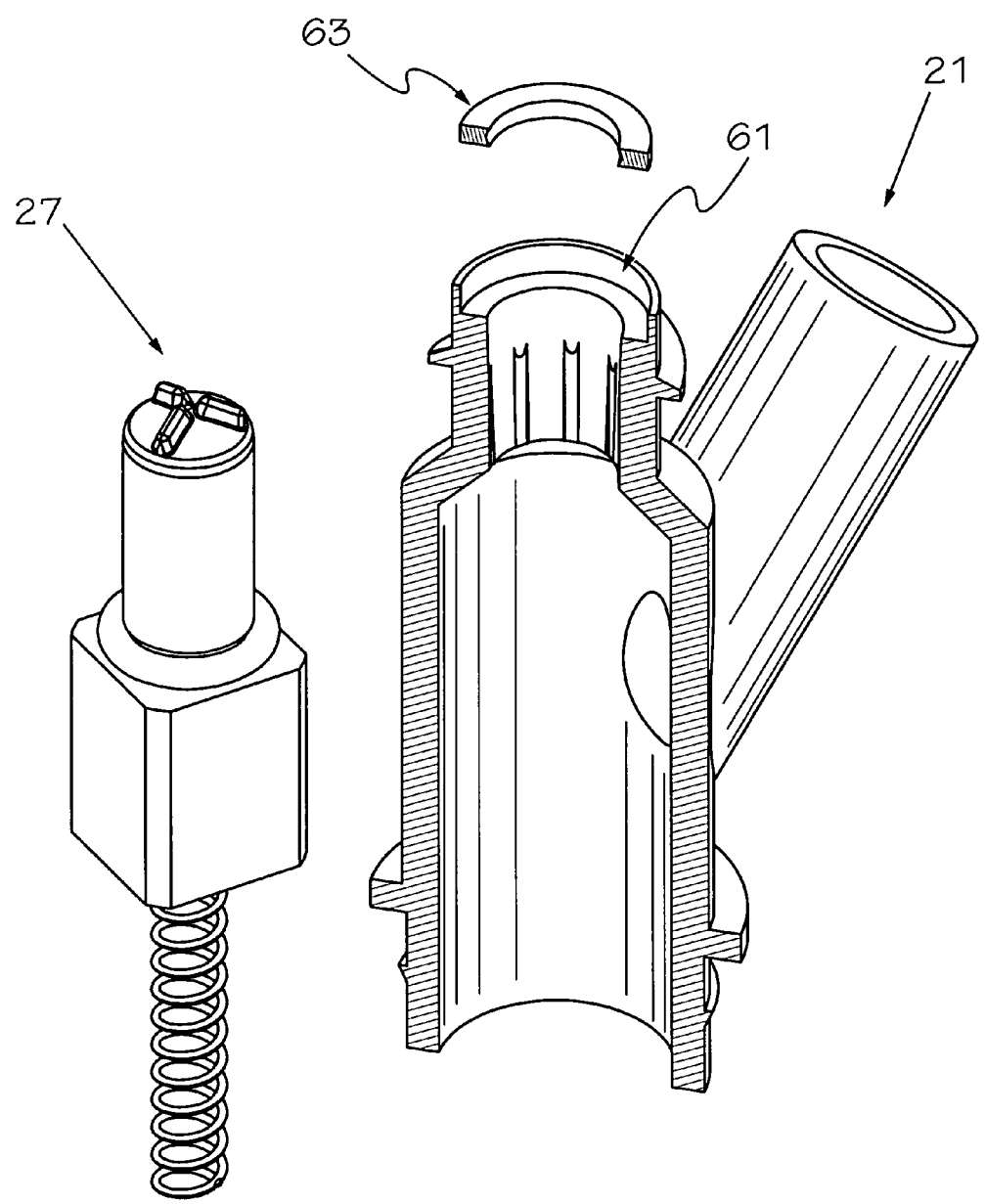
FIGS. 4 through 7 depict two alternative construction techniques for manufacturing a valve in accordance with the present invention.
Figure 5:
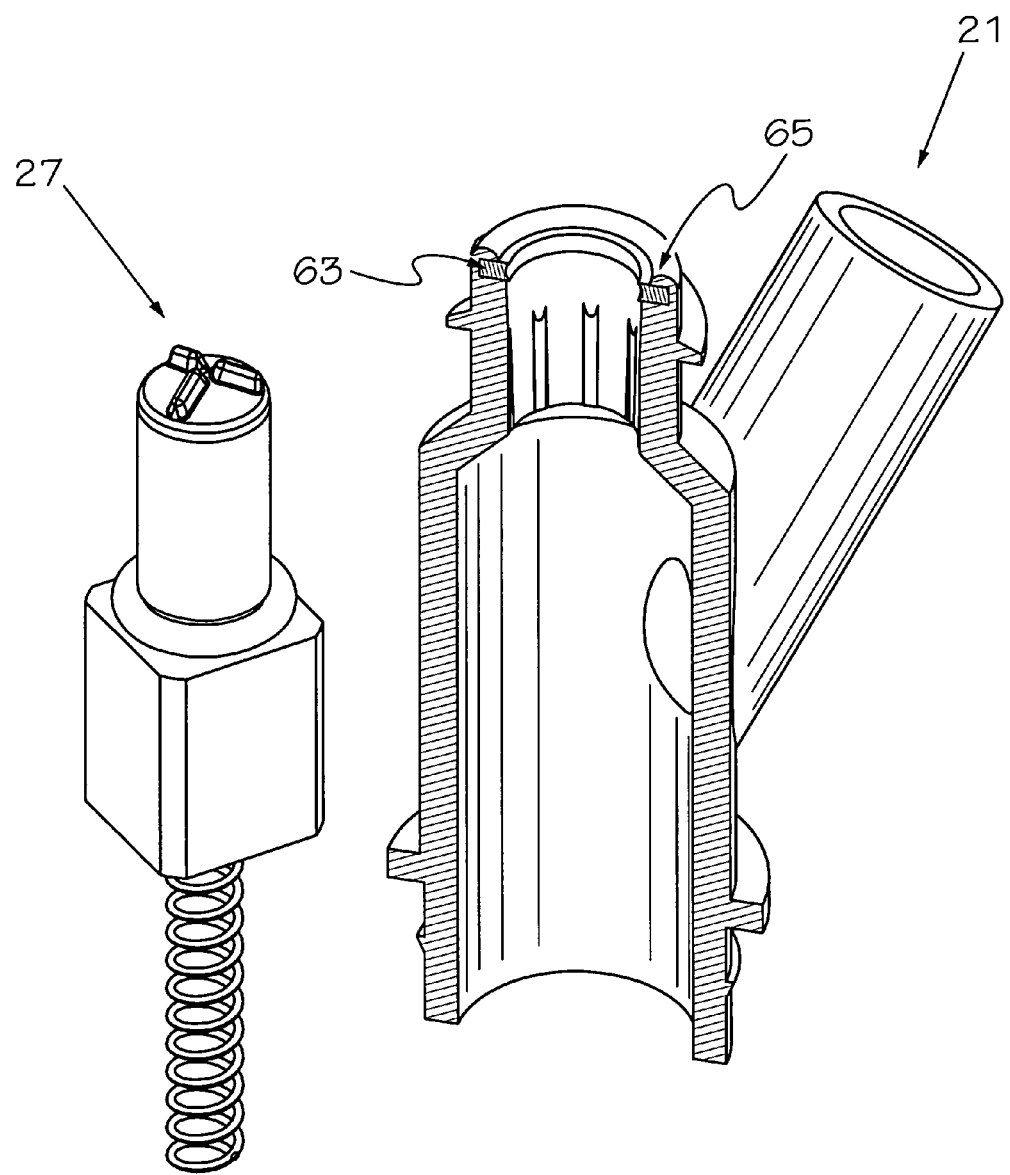
Figure 24:
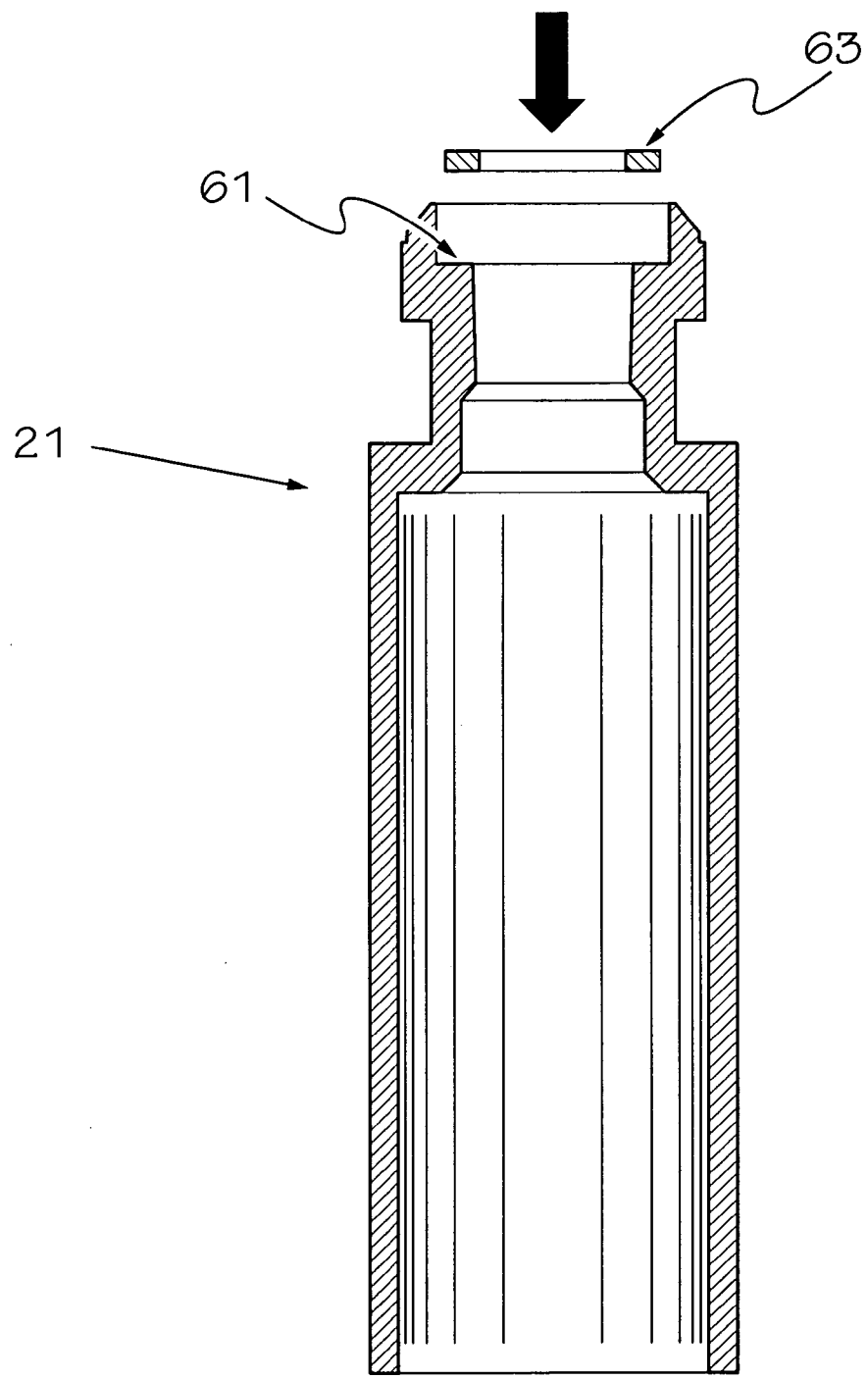
FIGS. 24 through 28 depict one process for constructing a valve in accordance with the present invention.
Figure 25:
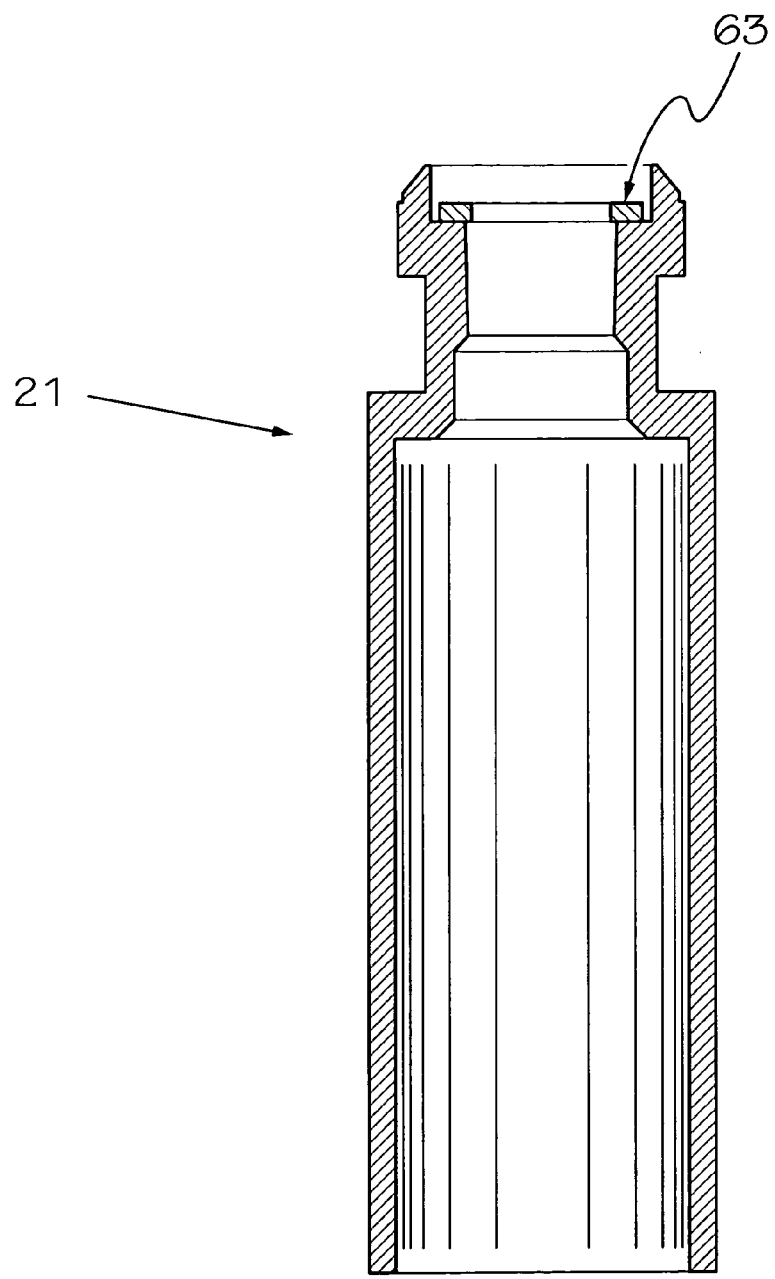
Figure 26:
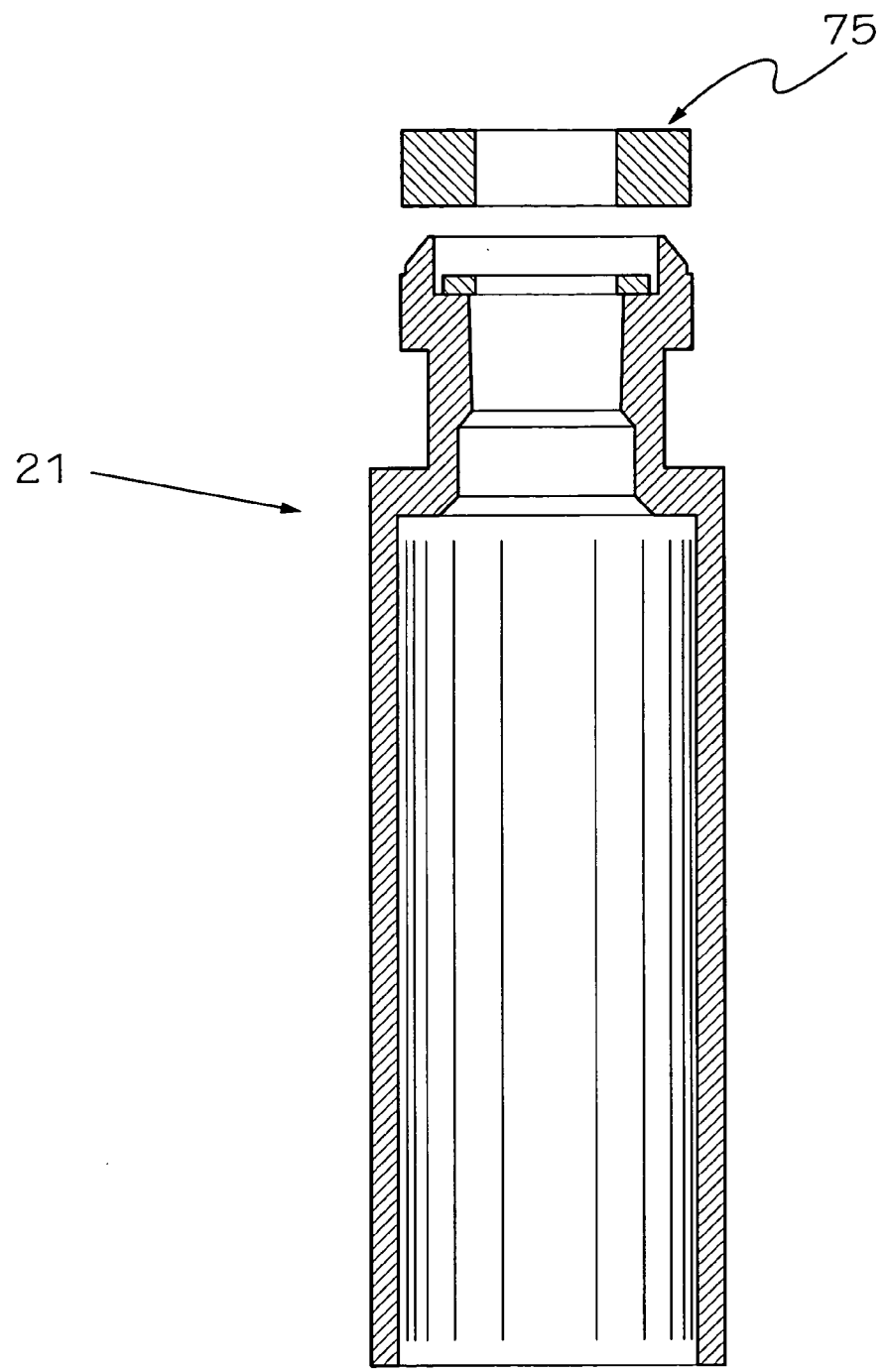
Figure 27:
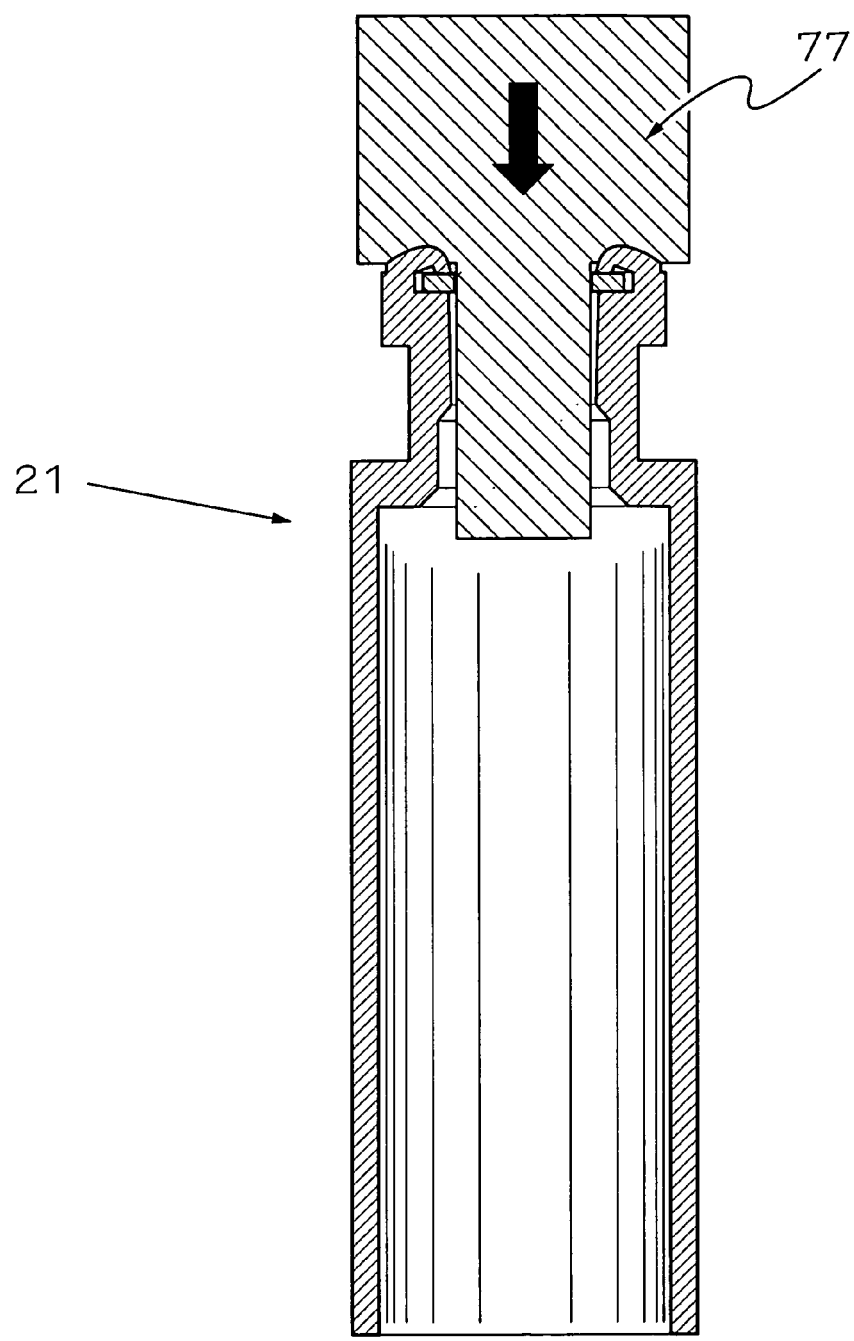
Figure 28:
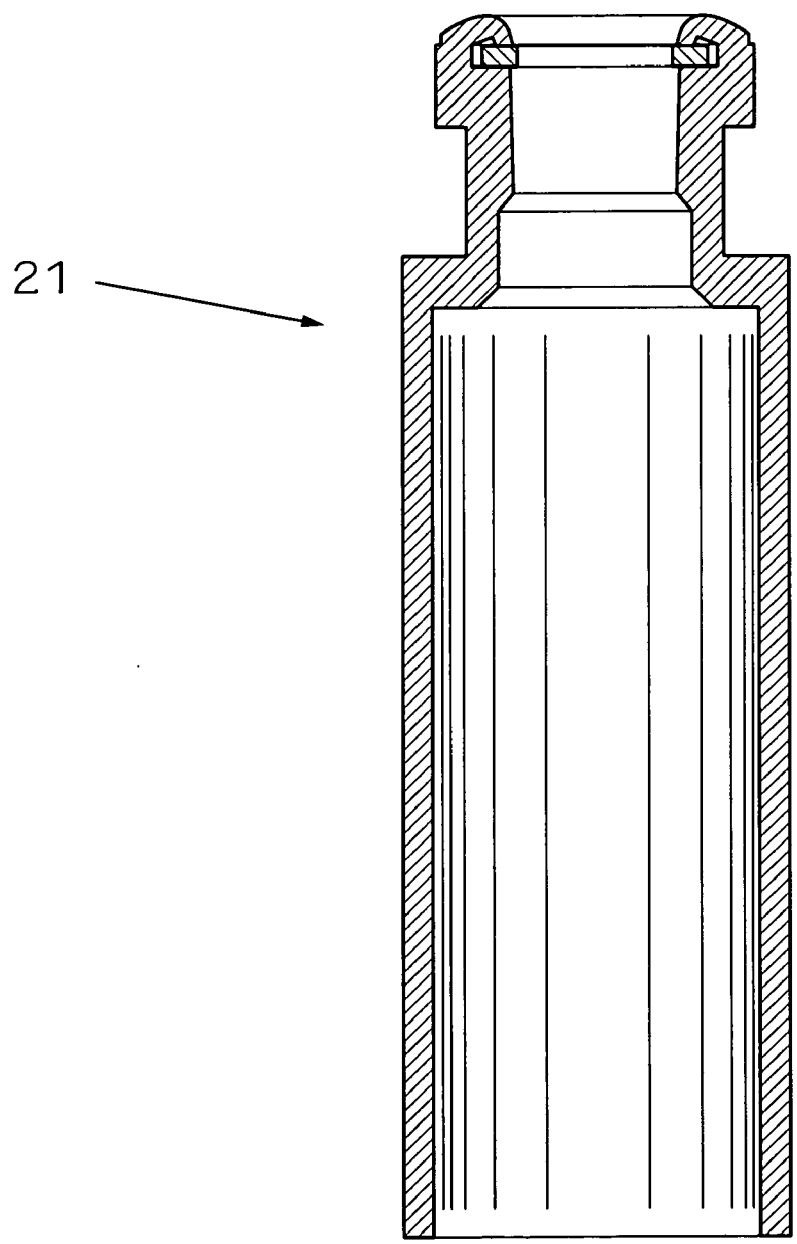
Figure 29:
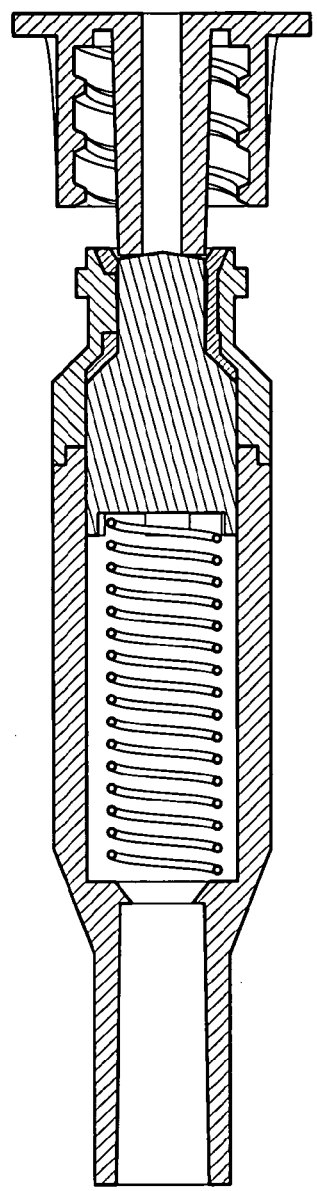
FIGS. 29–32 depict a second process for constructing a valve in accodance with the present invention.
Figure 30:
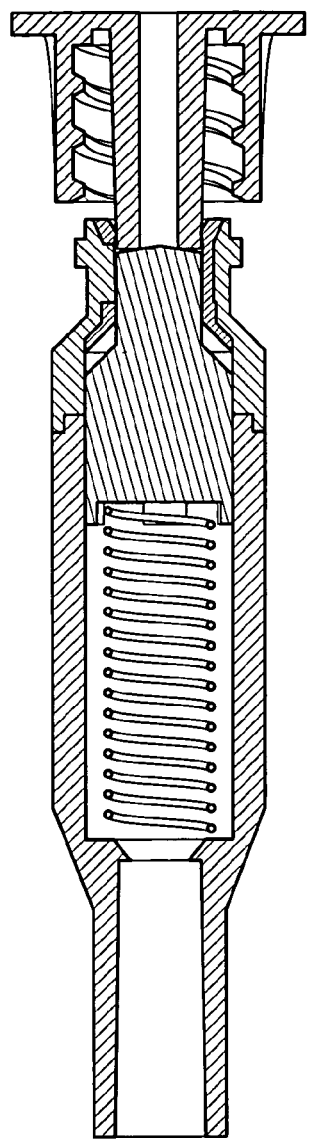
Figure 31:
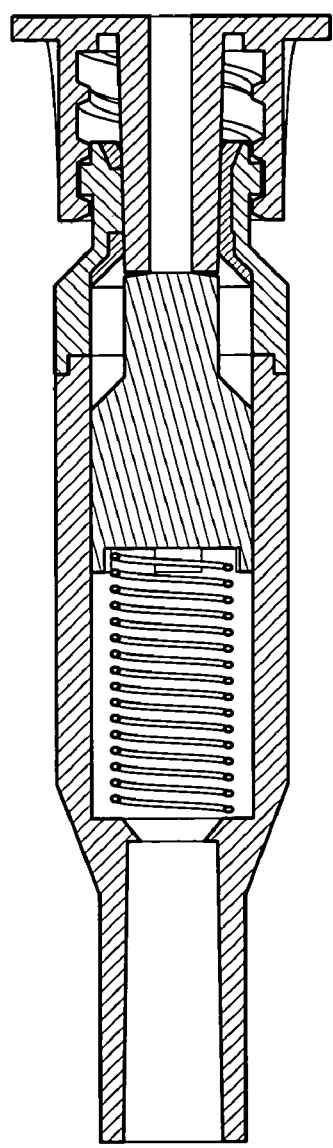
Figure 32:
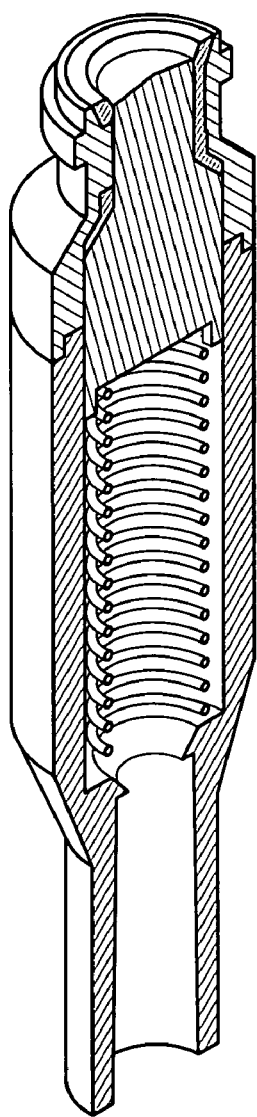

FIGS. 4 and 5 depict one alternative construction technique for the valve of the present invention. As is shown in FIG. 4, a uniform diameter opening 61 is provided at the upper end of valve body 21. Elastomeric barrier seal 63 is provided. During manufacturing, the elastomeric barrier seal is lowered into the upper end of valve body 21. Heat or ultrasound may then be applied to create a heat or ultrasound deformation 65 of the upper end of valve body 21 to secure elastomeric barrier seal 63. This is shown in FIG. 5. This manufacturing process is depicted as a series of steps in FIGS. 24–28. As is shown in FIG. 24, elastomeric barrier seal 63 is lowered into position relative to uniform diameter opening 61. FIG. 25 shows the elastomeric barrier seal 63 in place. As is shown in FIG. 26, a heater 75 is located adjacent the top of the valve housing 21, in order to heat up the material. Then as is shown in FIG. 27 a forming tool 77 is pressed into the heated part. The forming tool 77 shapes and cools the part into its final from which is shown in FIG. 28.

Figure 6:
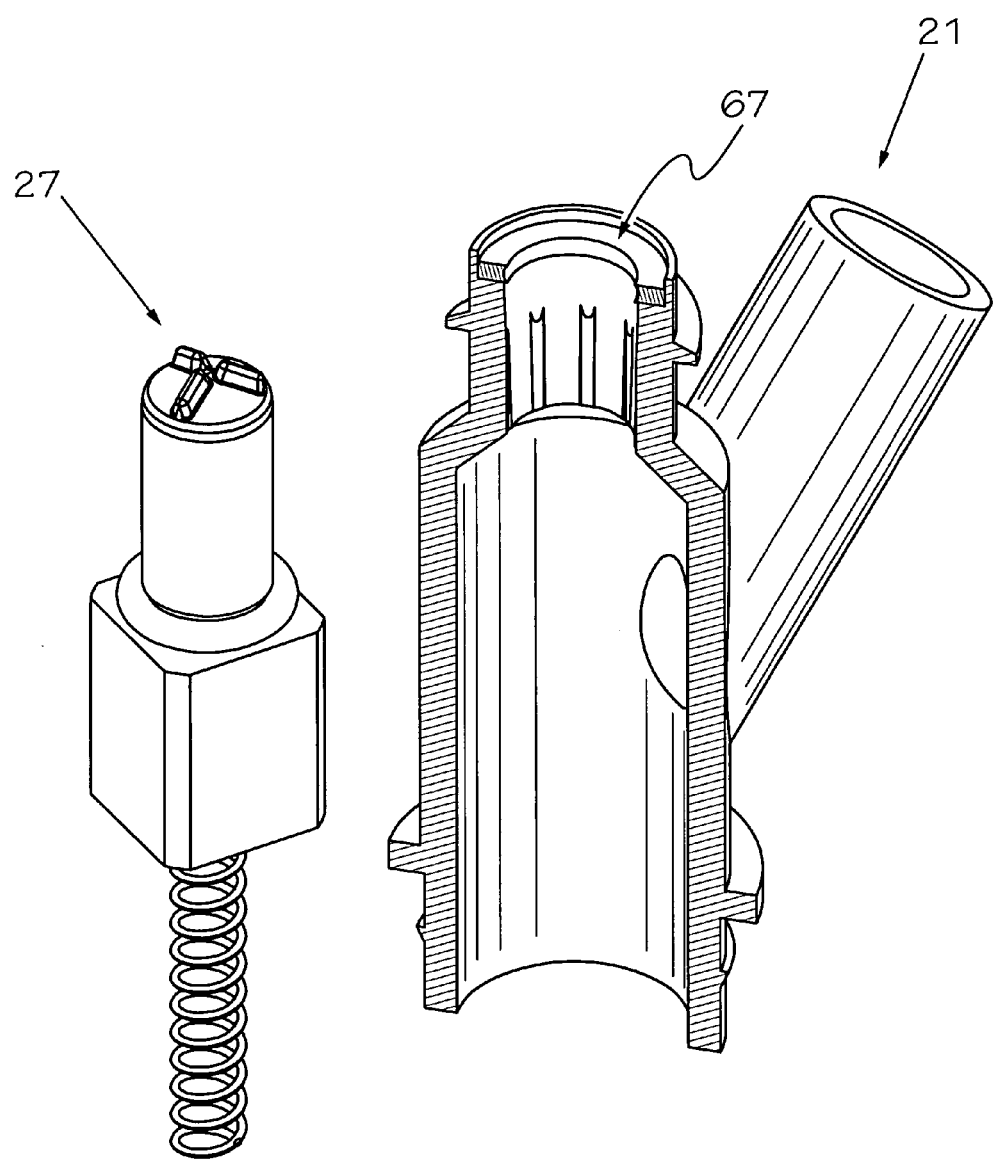
Figure 7:
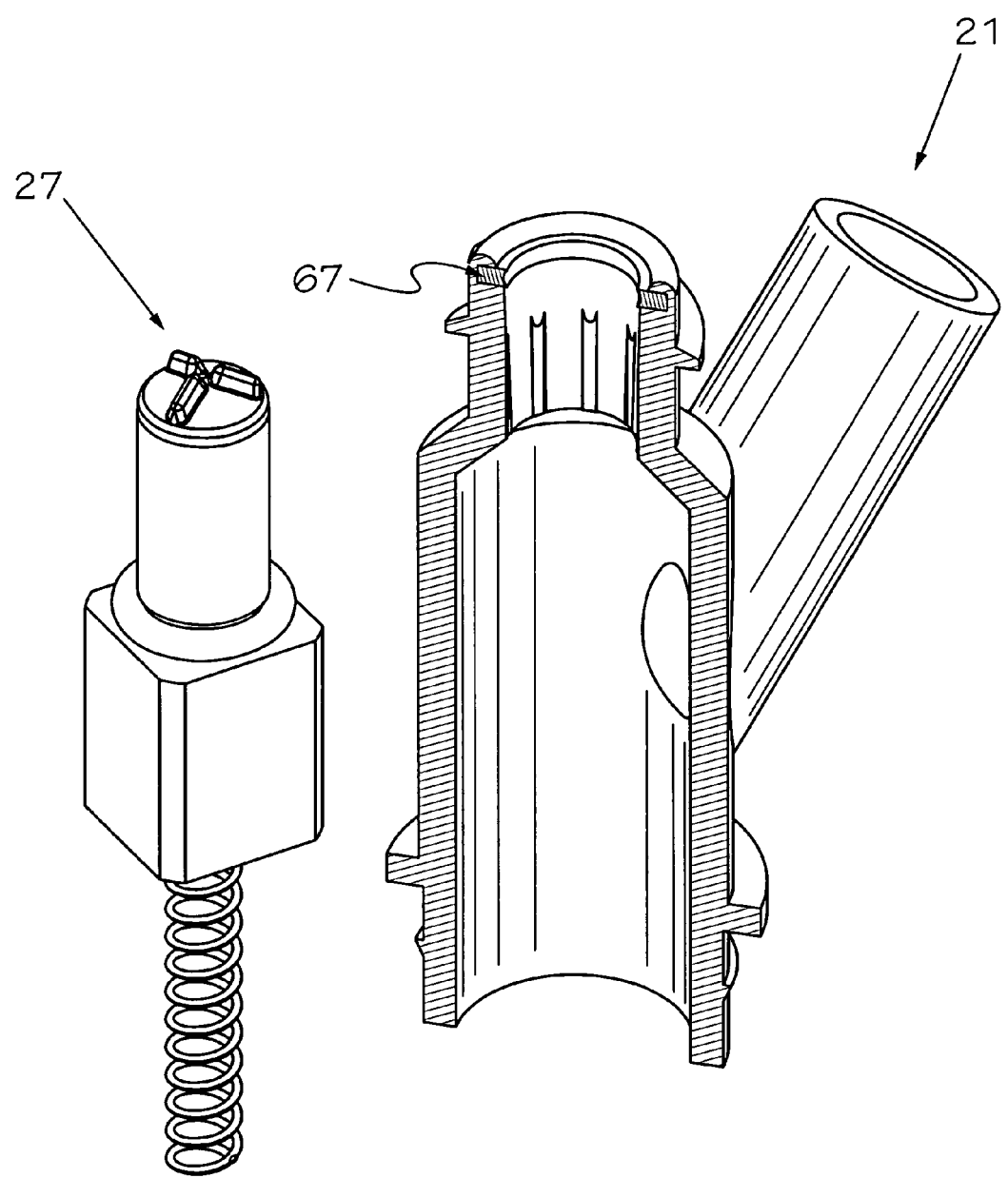

FIGS. 6 and 7 depict another alternative construction technique for the valve of the present invention. As is shown in FIG. 6, a double wall molding 67 may be utilized to secure elastomeric barrier in position. FIG. 7 depicts the valve in final assembled form.

Figure 8:
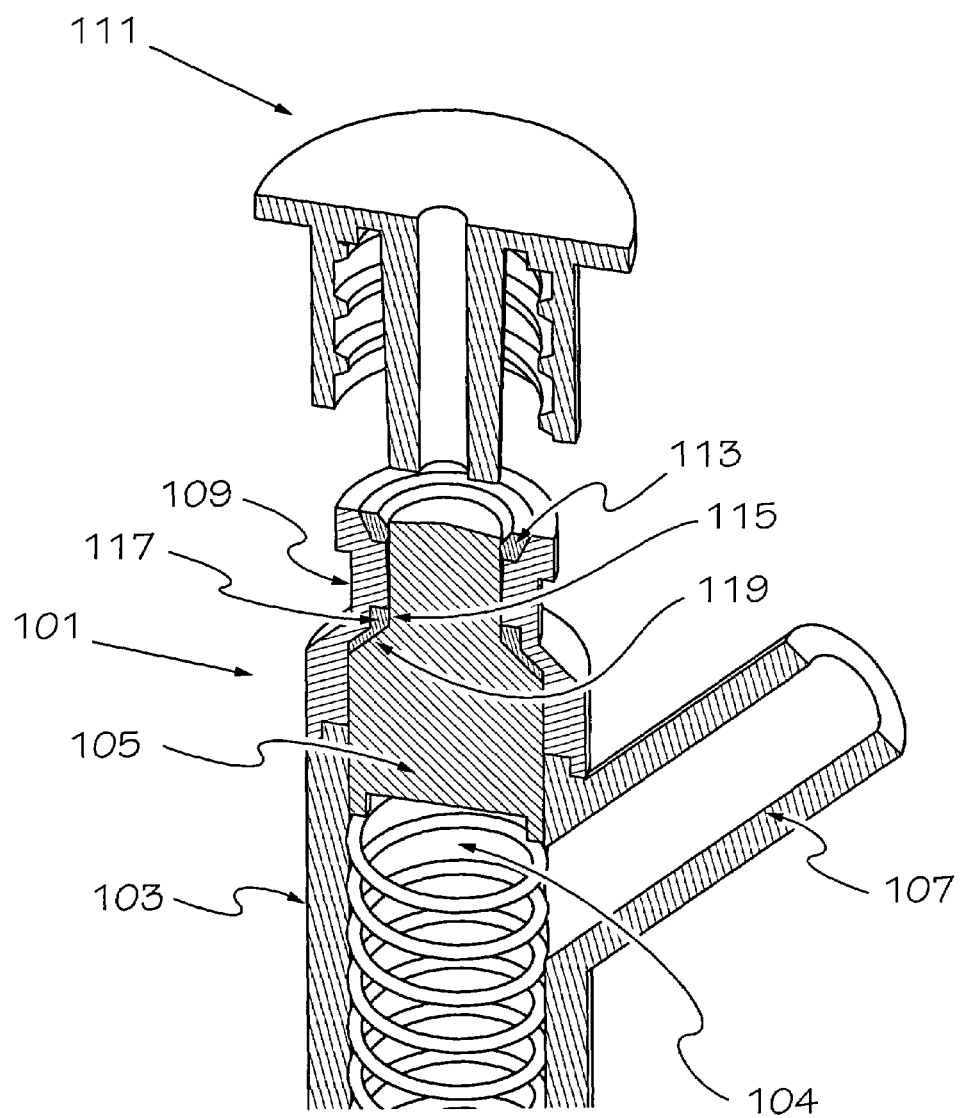
FIGS. 8 through 10 depict one embodiment of the present invention in which three sealing functions are performed by two seal structures which are carried by the valve body of the valve-device, as opposed to being carried by a movable piston member of the valve device.
Figure 9:
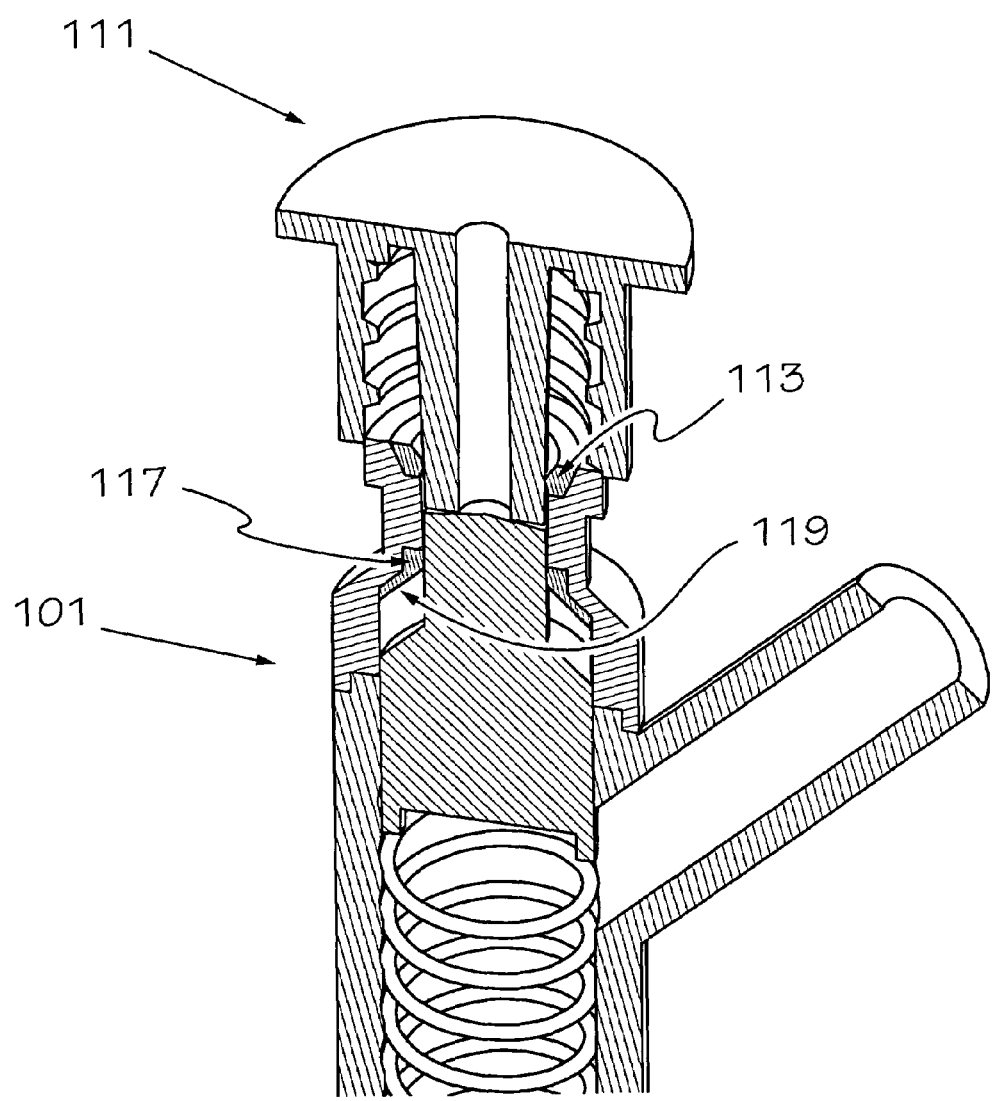
Figure 10:
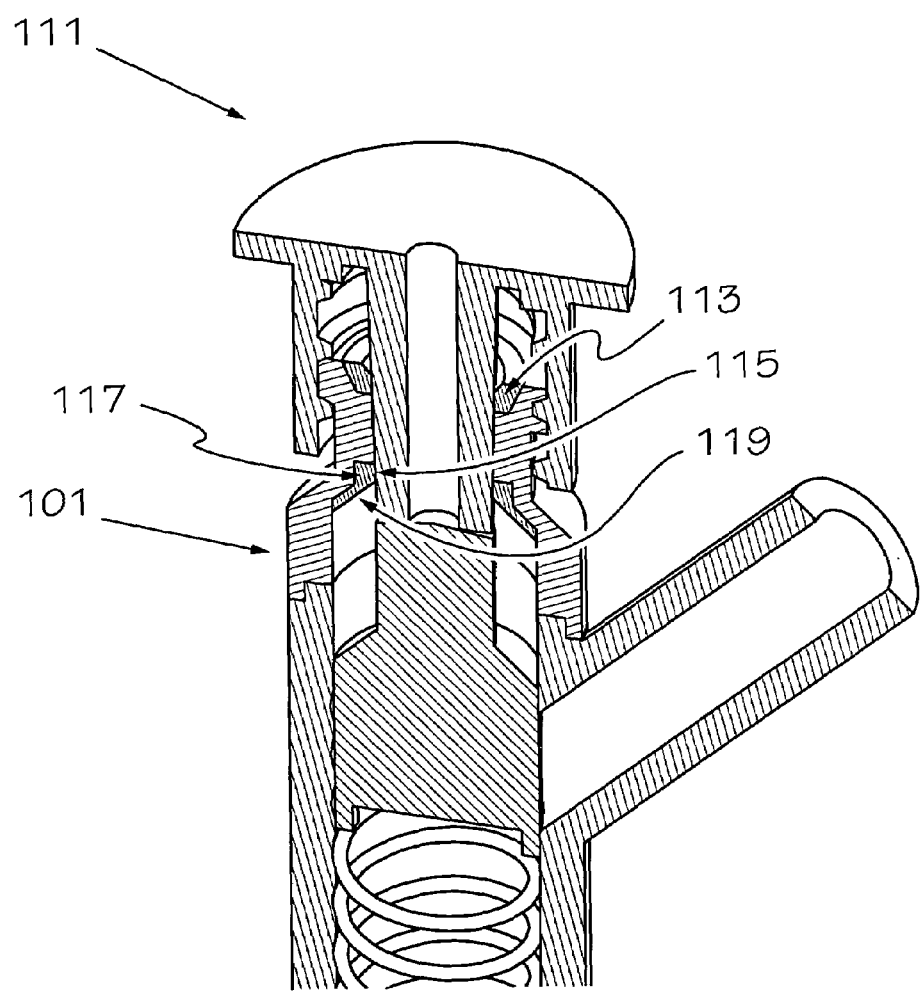

FIGS. 8 through 10 depict one embodiment of the present invention, in which an upper annular seal member is integral with the valve body and a second annular seal member is also integral with the valve body. Additionally, a third face seal is provided which is formed at the interface of a shoulder defined within the central fluid passageway and a shoulder which is formed on the piston member.

In this embodiment, the upper seal provides a primary seal, while the lower seal provides a backup sea, to prevent blood or fluid leakage when the piston is accidentally partially depressed. A face seal provides a "pressure seal".

In this embodiment, it is possible for the lower seal to be configured in a way so that it acts as a face seal and as the lower, backup seal. In this embodiment, since both seals can be integrally molded with the body in the same operation, the cost of assembling the moving seal to the piston is eliminated thus reducing manufacturing costs.

FIG. 8 depicts a valve 101, which composed of a valve body 103 and a piston 105. The valve defines a female luer 109 which is adapted to mate with a male luer connector 111. A central fluid passageway 104 is defined within valve body 103. A y-branch passage is connected to the central fluid passageway 104. This allows the mixing of fluids within the valve, and it is conventional.

The upper-most seal, or "top" seal is seal 113 which is integral with the valve body 103. Preferably it is an O-ring type seal which is formed from an elastomeric material, but which may be formed from other materials. It is carried in an annular cavity formed in the valve body 103 in the region of the valve 101 in which the male luer 111 first comes into contact with the female luer 109. A second, lower seal 117 is provided at a lower location relative to the upper seal 113. Preferably, the lower seal 117 includes an annular seal 115 which is carried by the valve body 103 in position proximate the change in diameter of the central fluid passageway 104 of the valve body 103. At this location a shoulder is defined by both the central fluid passageway 104 and the piston 105. A third, face seal is defined by the engagement of the piston shoulder and the cavity shoulder.

FIG. 8 shows the valve 101 in a fully closed condition. In contrast, FIG. 9 depicts the same valve 101 in a partially open condition. In this condition, the upper seal 113 is open, the lower seal 117 is still effective, and the face seal 119 is not providing a strong pressure seal at this time.

FIG. 10 depicts the same valve 101 in a fully open condition, with all three seals open.

Figure 11:
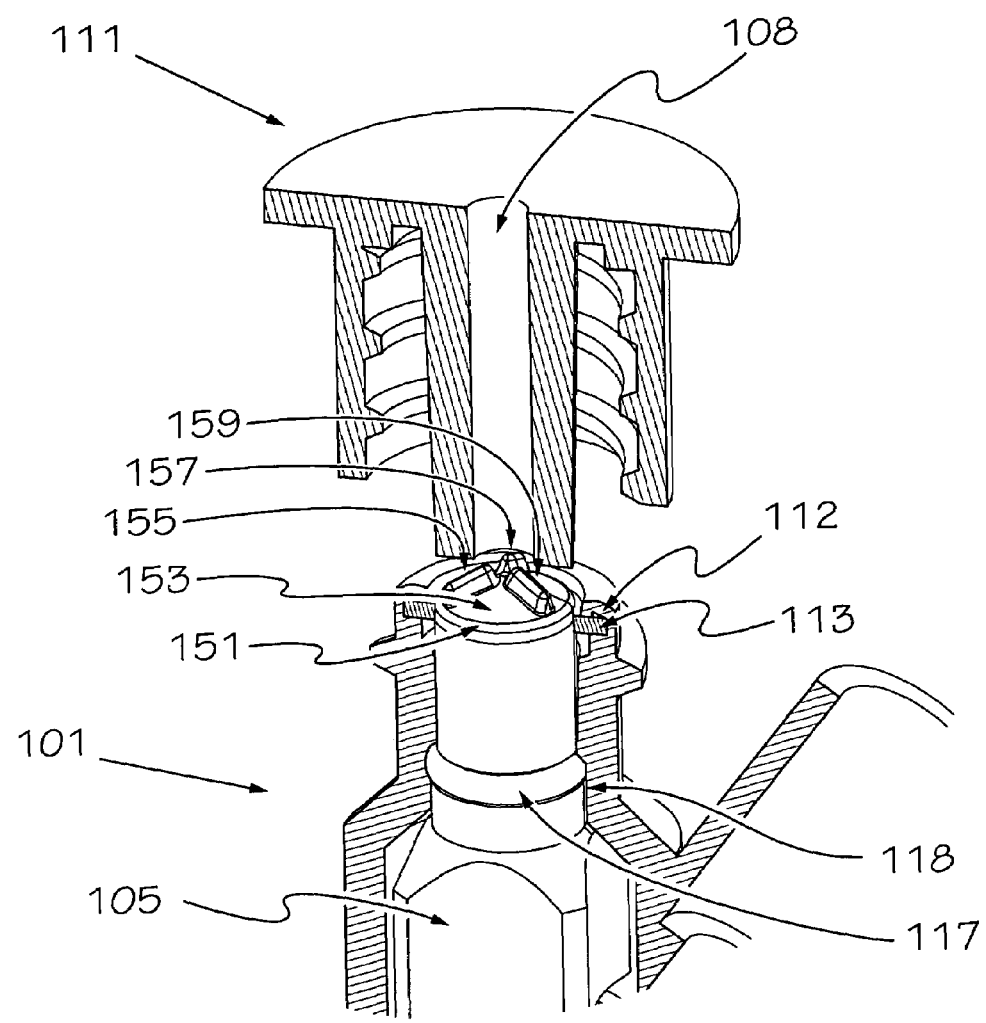
FIGS. 11 through 12 depict one feature of the preferred piston tip end of the valve device of the present invention.
Figure 12:
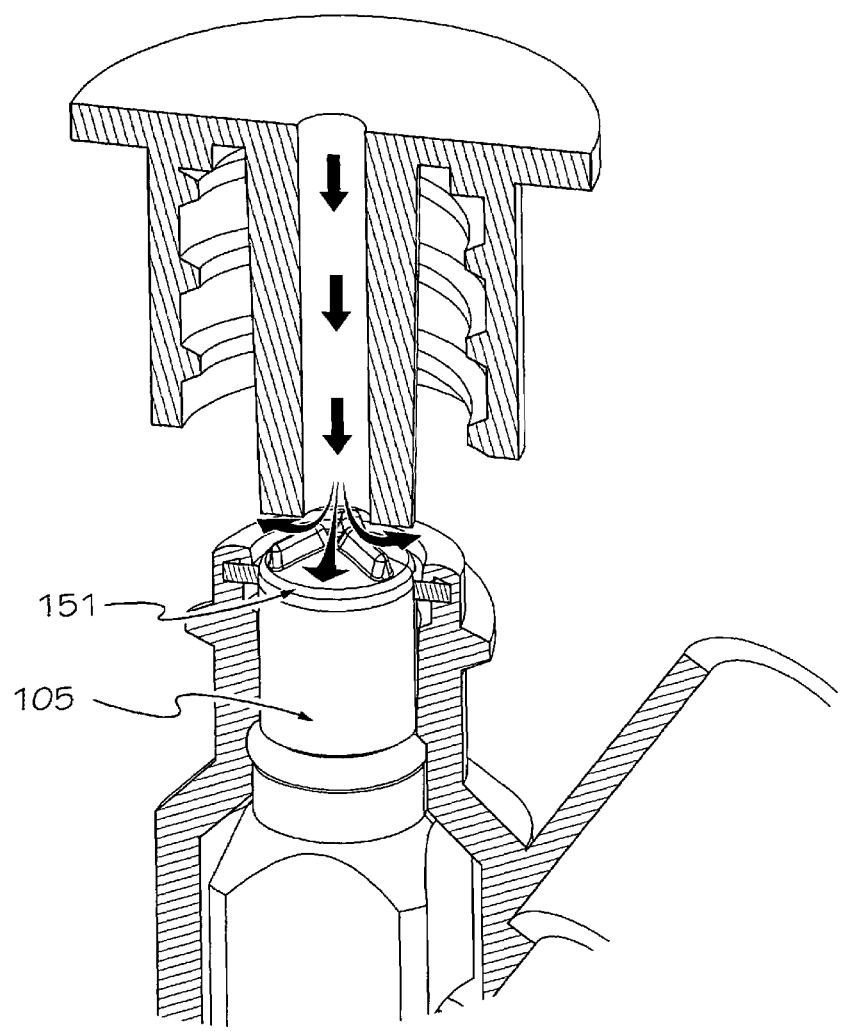

FIGS. 11 and 12 another embodiment of the present invention in which the lower valve is carried by the piston 105. In this embodiment, the face valve and the lower valve are separate structures. It also depicts another feature of the present invention which is carried at the tip 151 of the piston 105. This feature may be utilized with any embodiment of the present invention. Also, as is shown in FIG. 11, the valve body 105 includes seal cavity 112 which carries upper or "top" seal 113, and seal cavity 118 which carries lower seal 117.

Tip 151 is a slightly conical, domed-shaped surface 153, and it carries a plurality of raised ridges or "ribs", such as ribs 155, 157, 159. These ribs 155, 157, 159 extend along the direction of the conical surface and together form an apex which is generally centrally located relative to a centerline. The apex is adapted in size and shape to engage the central bore 108 of male luer 111. FIG. 12 depicts how fluid flows from the male luer over the tip 151 of piston 105. When properly configured, the ribs on the conical surface at the top of the piston contact the tip of the male luer and keep it a suitable distance from the surface to allow adequate flow between them. The conical tip ensures that, no matter which side the nurse approached the valve entrance, the tip of the male luer will not slide off, since it is meeting the rising conical surface of the top of the piston.

Figure 13:
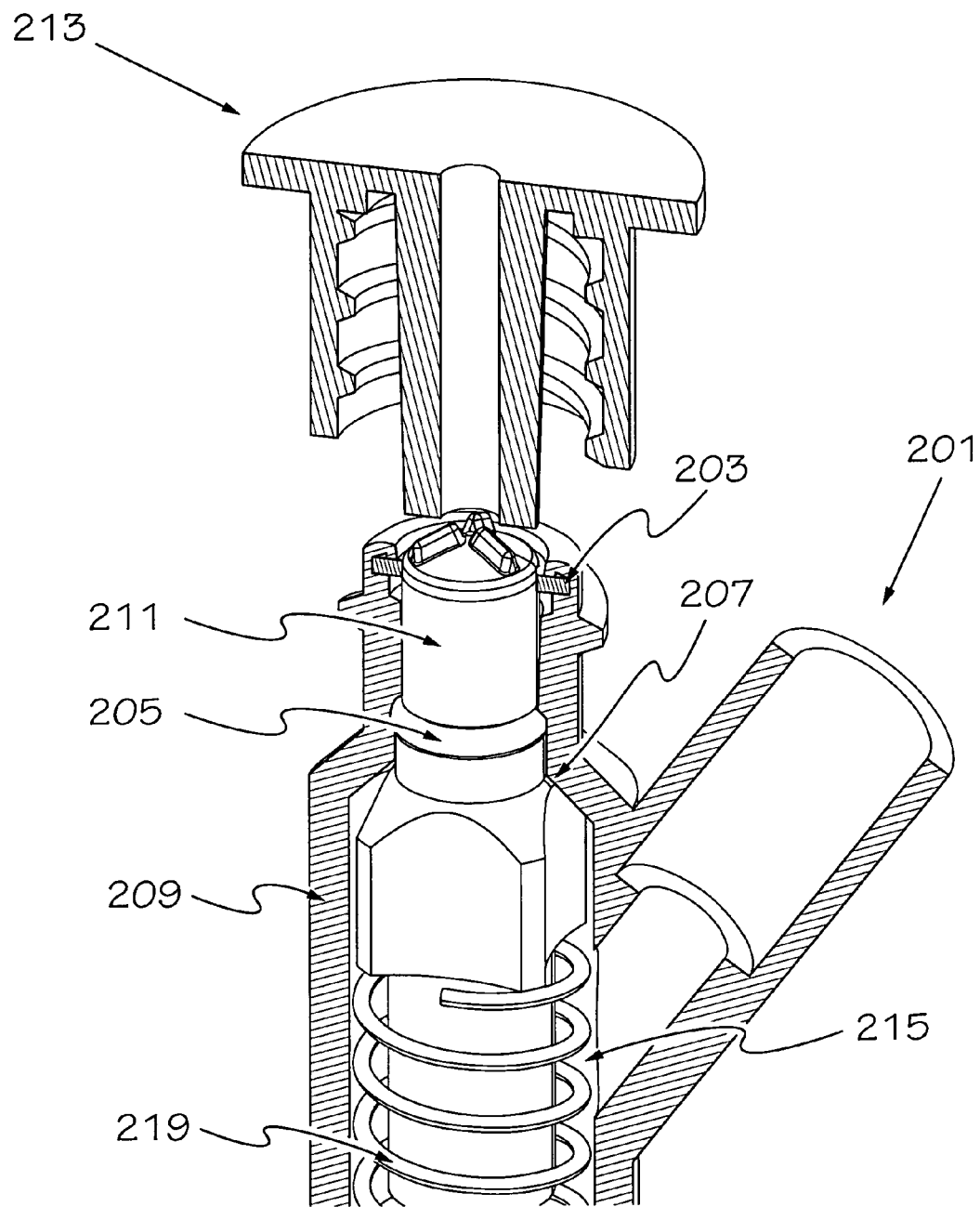
FIGS. 13 through 23 depict an alternative embodiment of the present invention in which one seal member is carried by the vale body and another valve member is carried by the piston member.

FIG. 13 depicts an alternative embodiment of the valve of the present invention in which the top seal 203 is carried by the valve body 209, the lower seal is carried by the piston 211, and the face seal 207 is formed at the shoulder-to-shoulder interface of the piston and the central fluid passageway 215 which is formed in the valve body 209.

Figure 14:
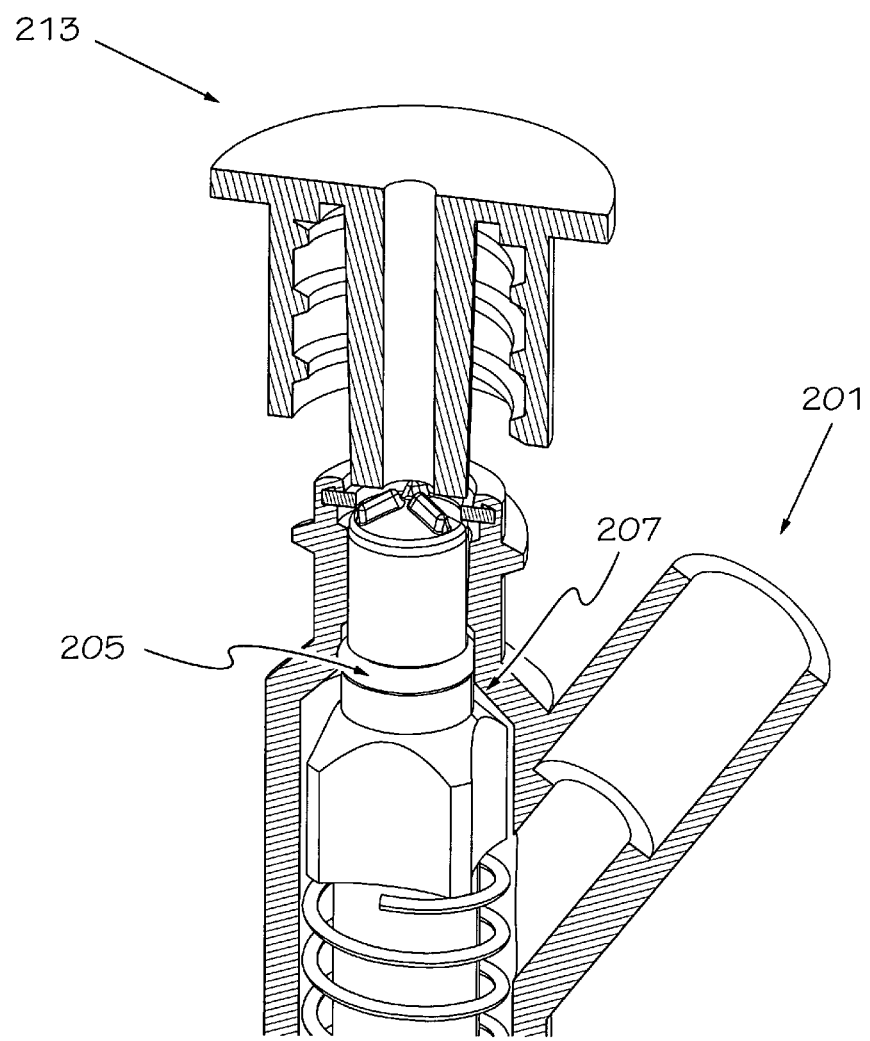
Figure 15:
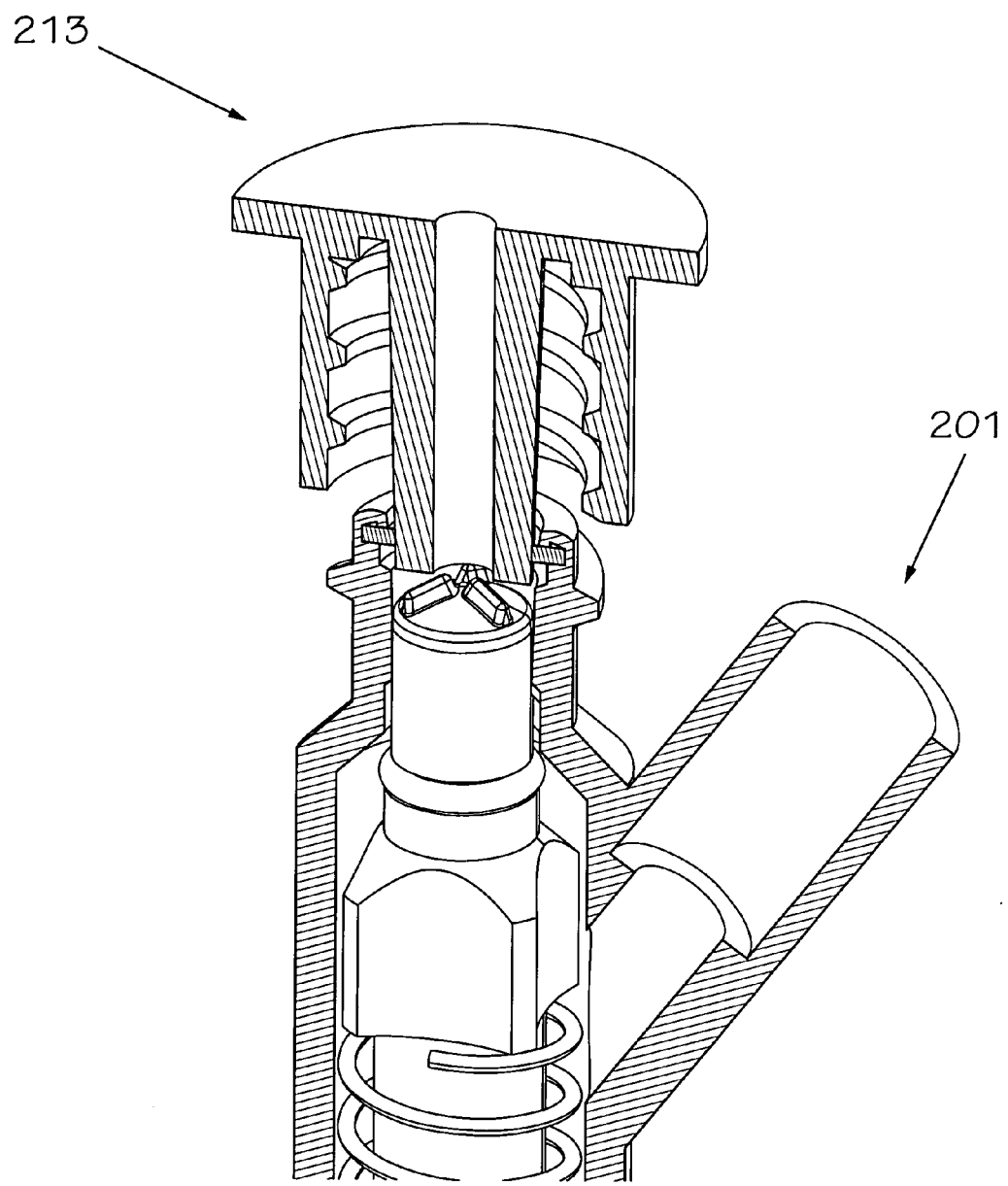

FIG. 14 depicts the valve 201 prior to opening. In this condition, the face seal 207 is now open, but lower seal 205 is still effective and preventing blood leakage. FIG. 15 depicts the valve 201 fully open.

It is possible that the top a of piston may be depressed by accident, either by the patient or medical staff. Since the medical valve is connected to the patient's bloodstream, it is a very undesirable outcome. Such an occurrence can cause blood loss or the entry of bacteria into the patient.

The valve of the present invention is designed to include a face seal which in the closed condition resists high pressures. As soon as the piston is depressed, this seal is no longer effective. This is useful because many medical procedures require that pressure be applied to the patient's vascular system. This can occur in the injection of dyes or medicines. In the preferred embodiment, the seal element is an O-ring seal which serves as the lower backup seal and the face seal. The backup seal remains in contact with the inner diameter of the valve housing for a brief interval after the upper seal is opened; this ensures that the valve is not opened inadvertently due to accidental contact.

Figure 16:
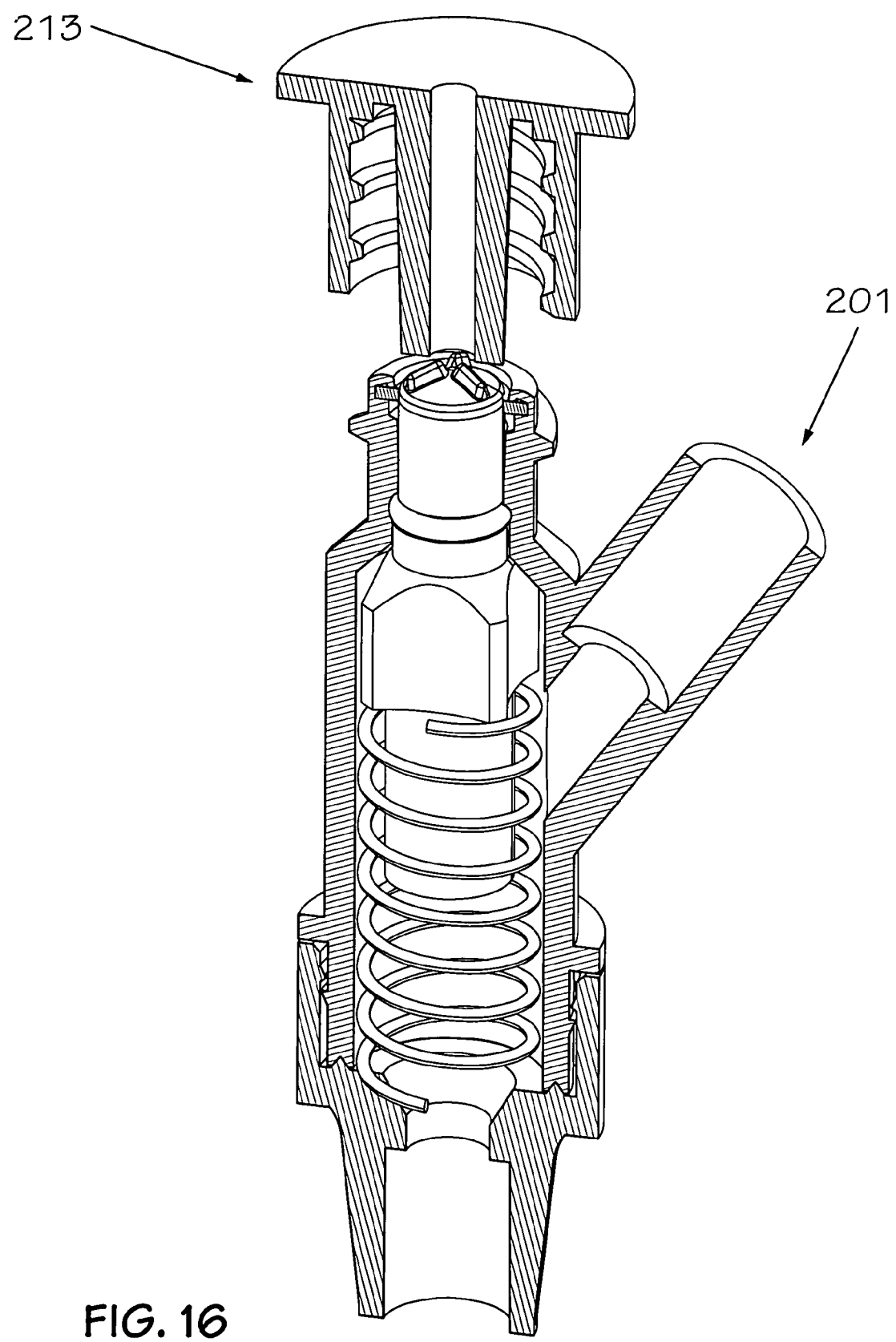
Figure 17:
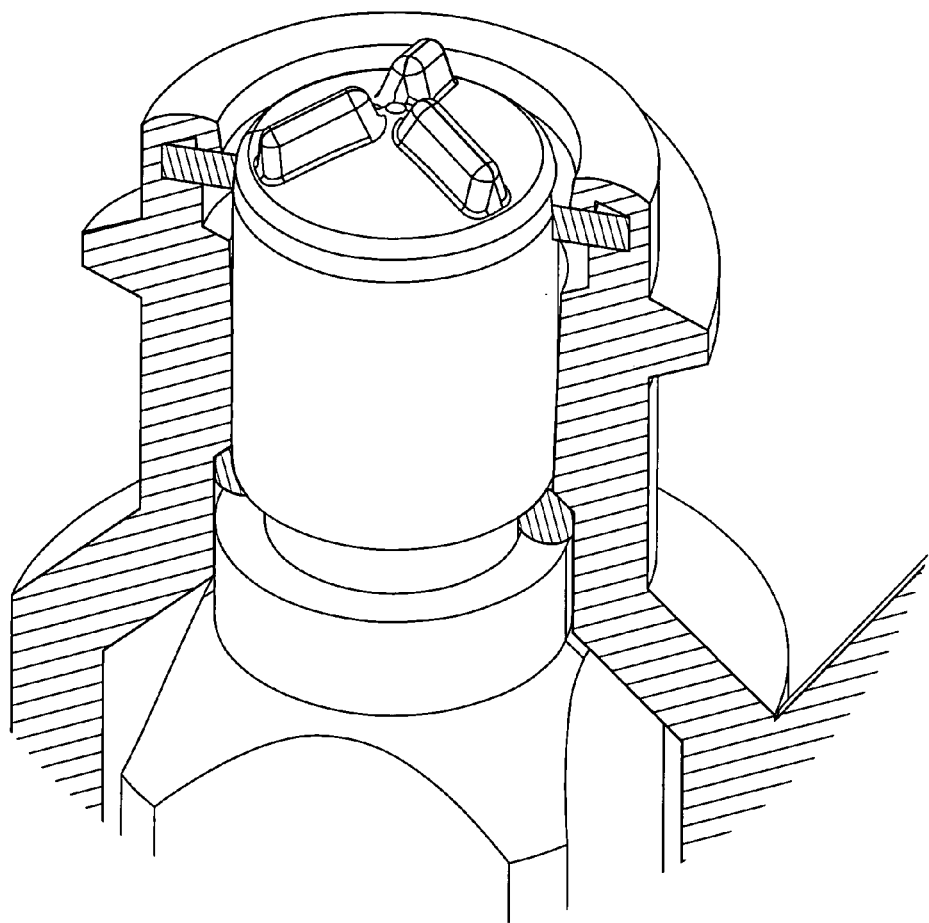
Figure 18:
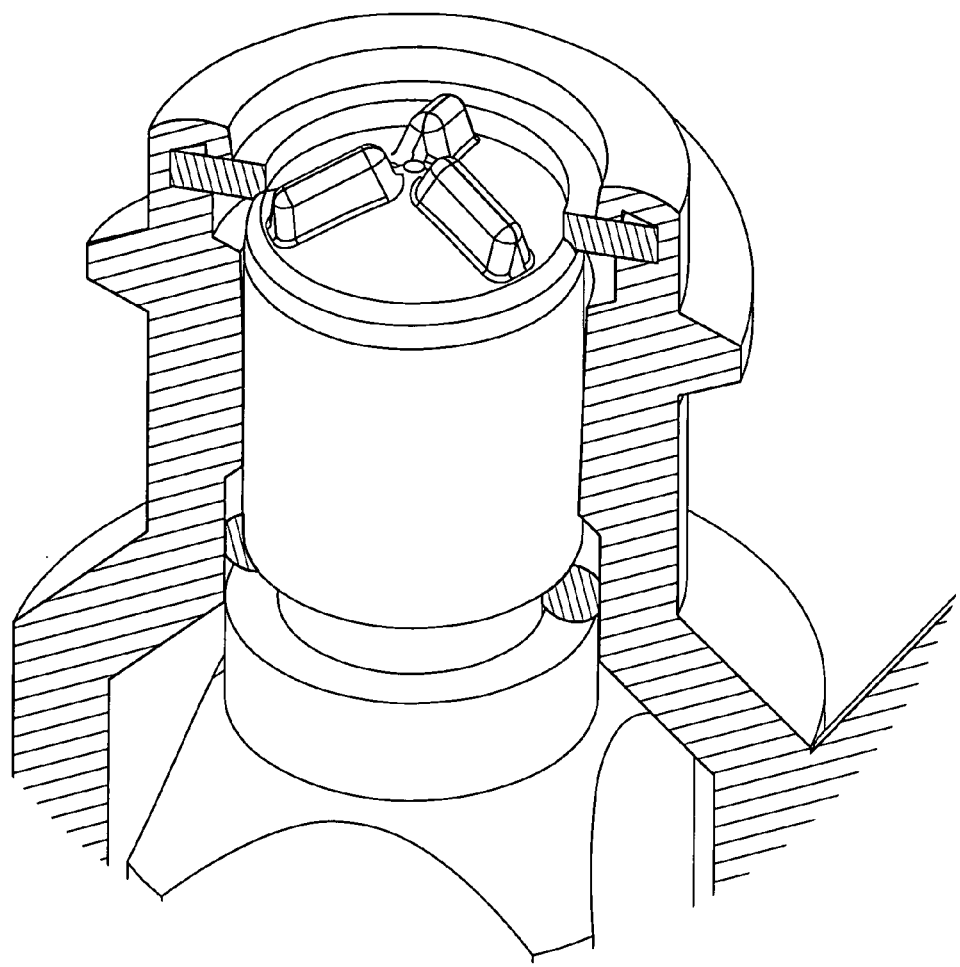
Figure 19:
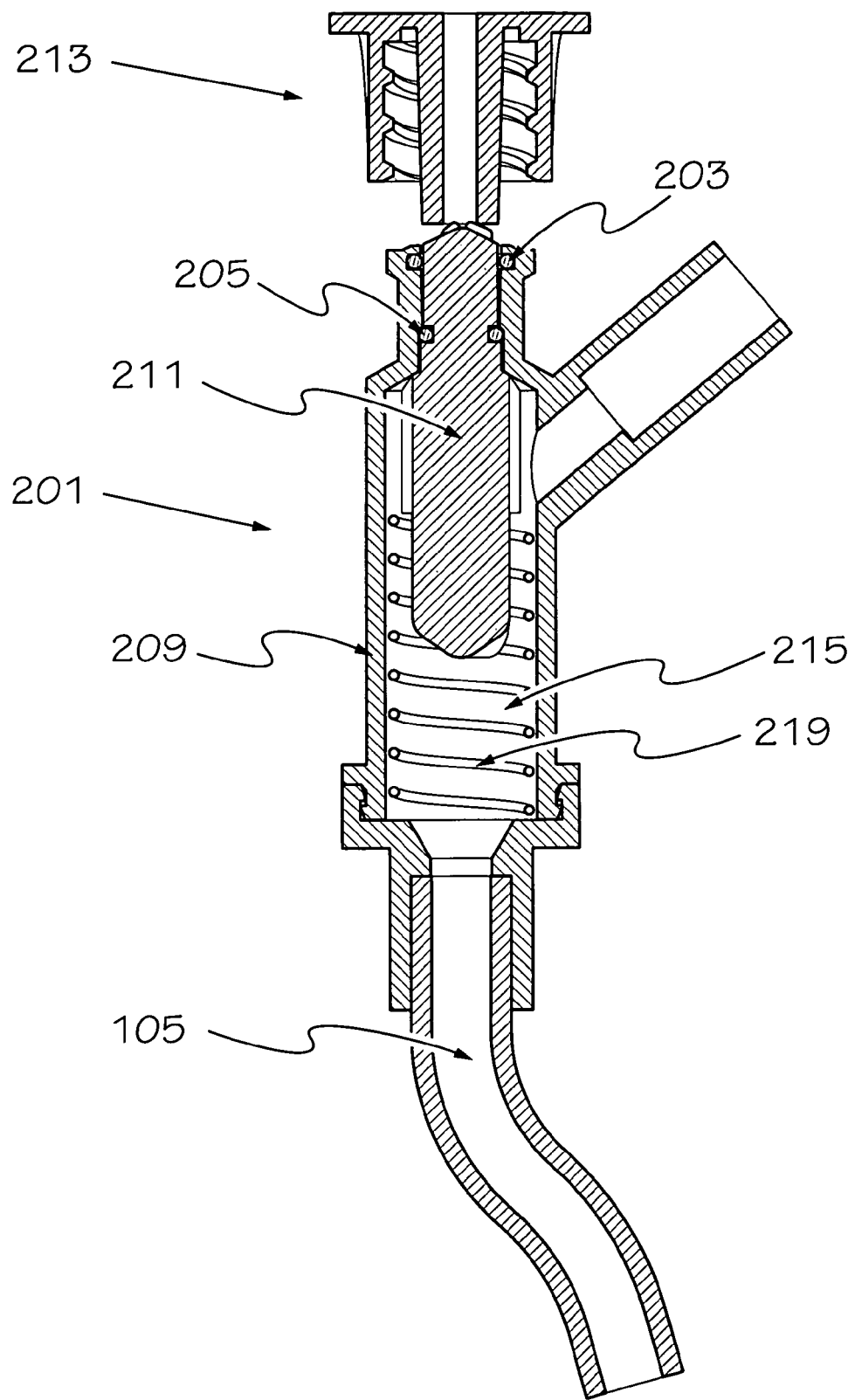

FIGS. 16 through 23 provide more detail about this embodiment. FIGS. 16 through 18 are exploded and partial longitudinal section views of valve 201. FIGS. 19 through 23 are longitudinal section views of the same valve. FIG. 19 depicts the male luer 213, the valve 201, the piston 217, the body 211, the spring 219, the central fluid passageway 215, the top seal 203 and the lower seal 205.

Figure 20:
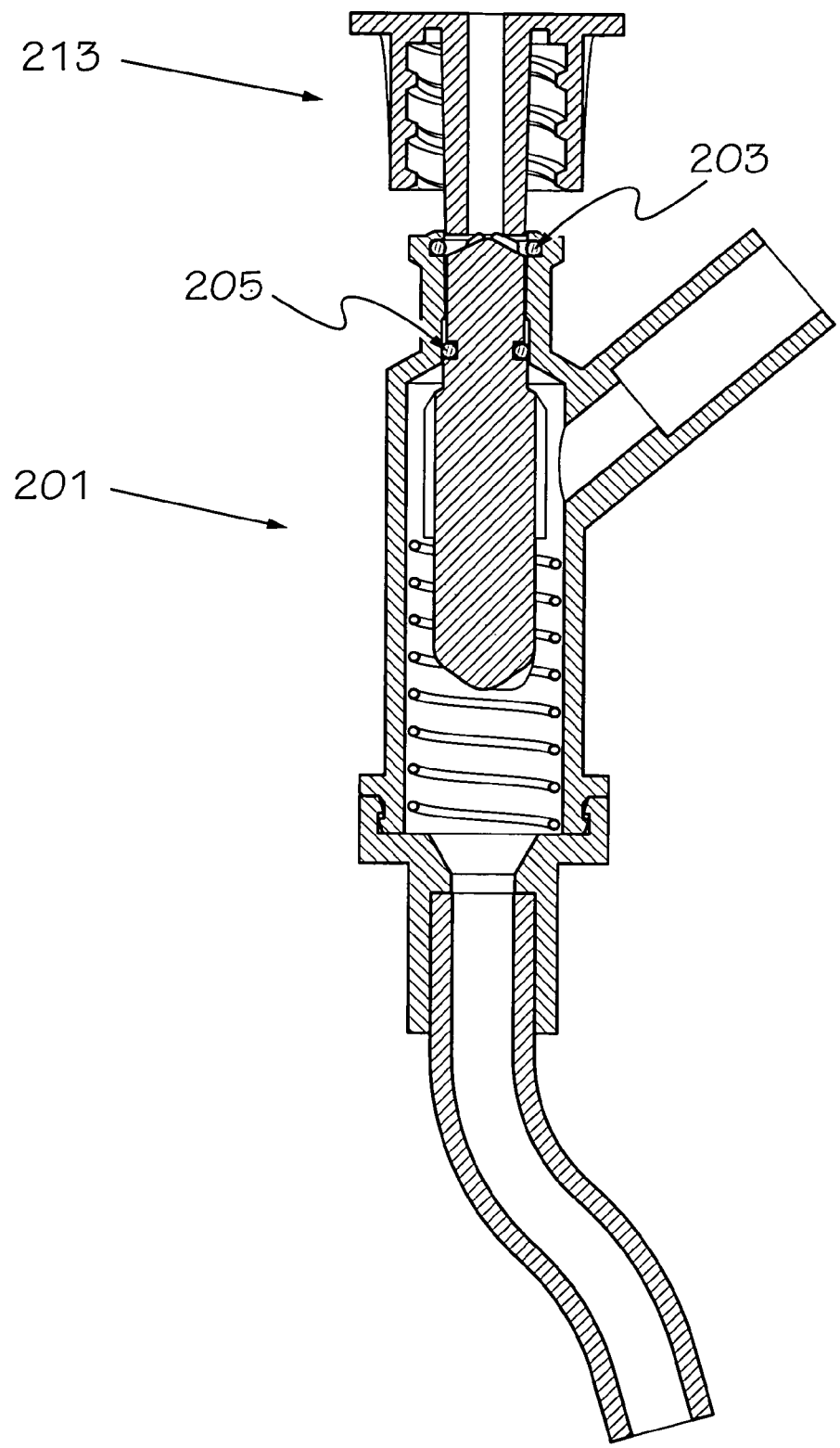
Figure 21:
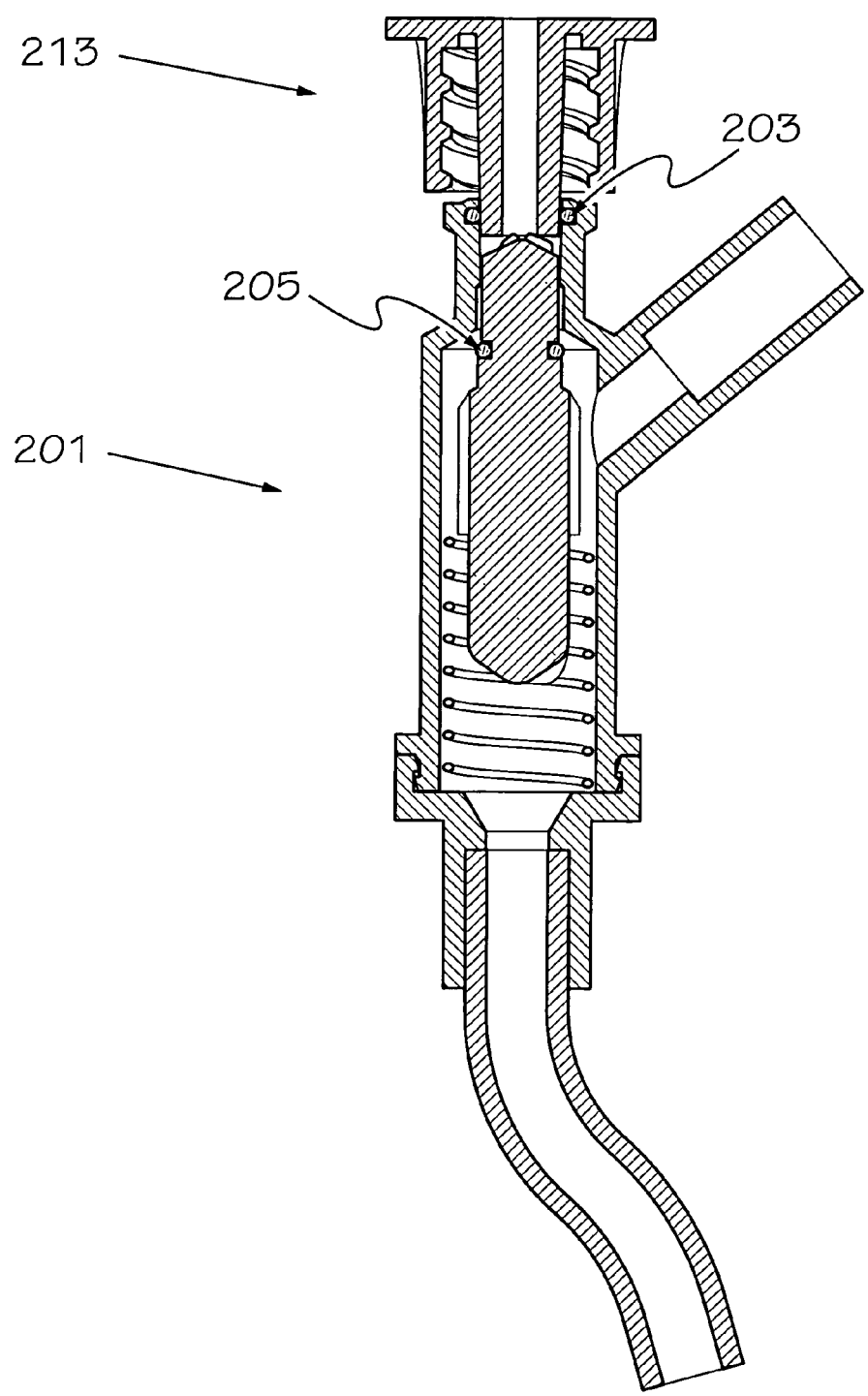

FIGS. 19 through 21 depict the valve 201 in three operating conditions: fully closed, partially open, and fully open. FIG. 19 depicts the valve fully closed. Note that O-ring seal cavity is formed in the upper portion of valve body 211, and an O-ring seal is disposed therein. Together this forms upper or "top" seal 203. Additionally, an O-ring seal cavity is formed on piston 205 and an O-ring is disposed therein. Together these form lower seal 205. When the valve 201 is fully closed, both O-rings make sealing contact with the inner surface of the valve body, so two seals are formed. Additionally, there is a face seal formed between the piston and the valve body. FIG. 20 depicts the valve 201 in a partially open condition. In this condition, the top seal 203 is "broken" but the lower seal 205 is still intact. The face seal is now less effective. In the view of FIG. 21, the valve 210 is in a fully open condition, as top seal 203 and lower seal 205 are broken, and there is no face seal in place.

Figure 22:
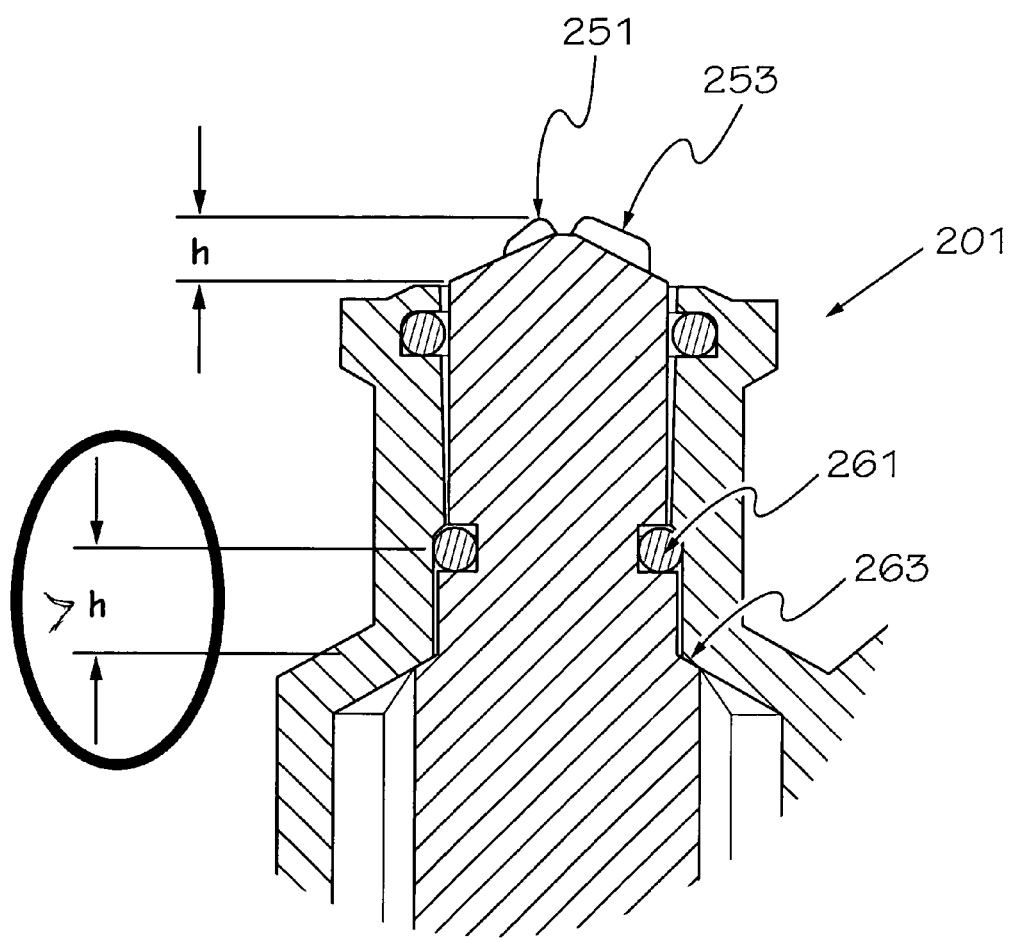
Figure 23:
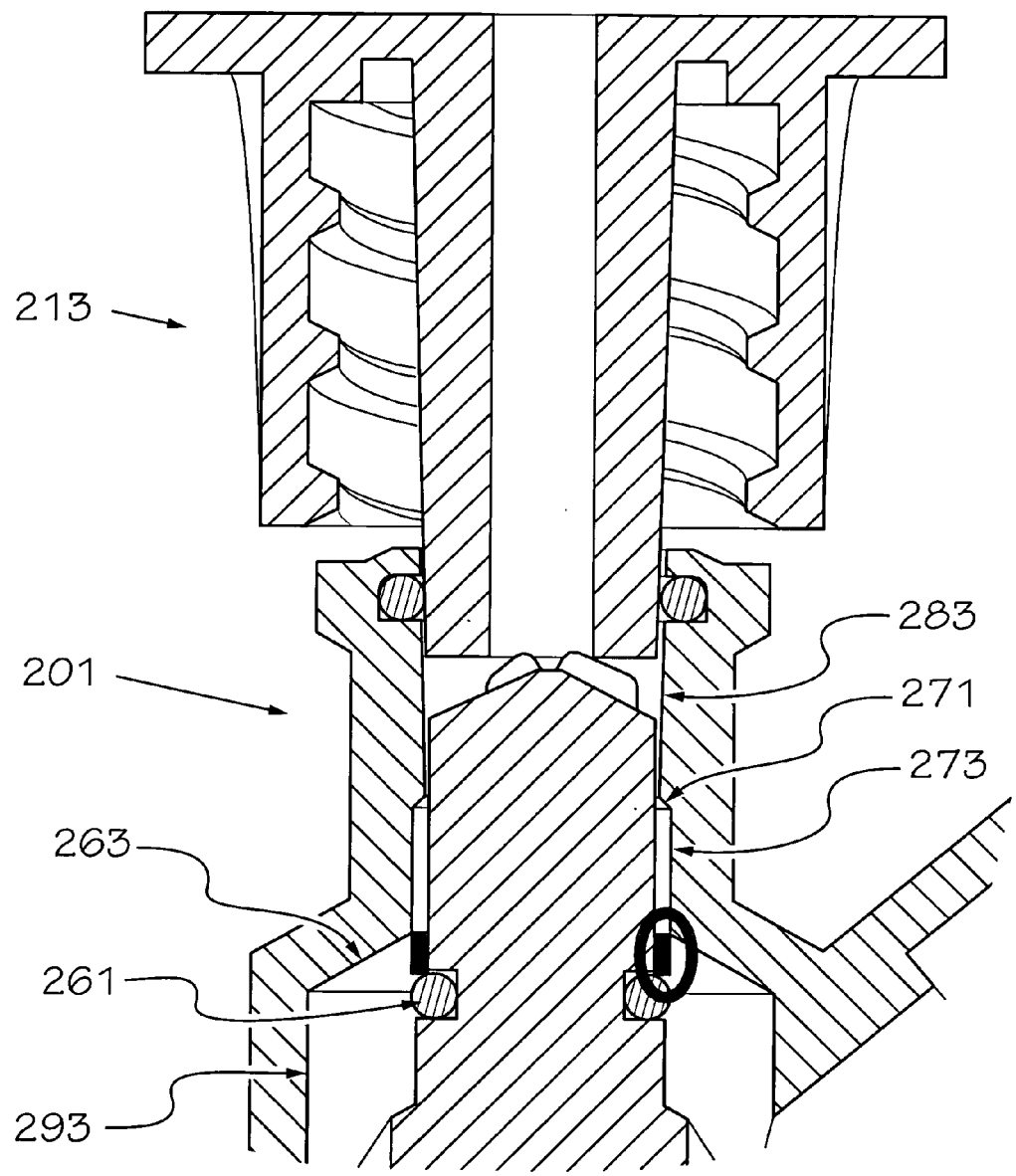

FIGS. 22 and 23 depict details concerning the dimensions of the piston and location of the seals necessary to accomplish the present invention. As is shown in FIG. 22, the distance from the top of ribs 251, 253 is "h"; accordingly, the distance from the middle of O-ring 261 and shoulder 263 is less than "h". This ensures that the lower seal is still intact until after the first seal is broken. As is shown in FIG. 23, for proper flow to occur, the piston must be depressed a minimum of "h" plus "Ma", wherein Ma is the annular, desired flow area. For the proper flow to be obtained, and for proper luer retention, the piston must be depressed an minimum of "Ma" plus "Mz", wherein Mz is the minimum male luer depth in accordance with the specifications.

FIG. 23 can be utilized to disclose the face seal of the present invention. As is shown, two shoulders are formed in the inner surface of the valve body. One is shoulder 271 which is a transition between surface 283 and surface 273. The second is shoulder 263 which is the transition between surface 273 and surface 293. O-ring is adapted to engage surface 273 and form a seal with it. Also, O-ring 261 will engage shoulder 271 and form a face seal with it.

Although the invention has been described with reference to a particular embodiment, this description is not meant to be construed in a limiting sense.

Various modifications of the disclosed embodiments as well as alternative embodiments of the invention will become apparent to persons skilled in the art upon reference to the description of the invention. It is therefore contemplated that the appended claims will cover any such modifications or embodiments that fall within the scope of the invention.

What is claimed is:

1. A medical valve, comprising:
   a valve body having a central fluid passageway defined therein;
   a movable piston located within said central fluid passageway;
   a first annular seal mounted on said valve body and engaging said movable piston; and
   a second annular seal mounted on said valve body and engaging said movable piston, said second annular seal having a first sealing surface defining a face seal surface engaging said movable piston and a second sealing surface, angled with respect to said first sealing surface, engaging said movable piston.

2. A medical valve according to claim 1 and wherein a shoulder is defined in said central fluid passageway and a corresponding shoulder is defined in said movable piston, and said face seal surface engages said shoulder of said movable piston and said shoulder of said central fluid passageway.

3. A medical valve according to claim 2 and wherein said face seal surface only engages said shoulder of said movable piston when said medical valve is closed.

4. A medical valve according to claim 1 and wherein said face seal surface only engages said movable piston when said medical valve is closed.

5. A medical valve according to claim 1 and wherein said second sealing surface engages said movable piston at least when said medical valve partially open, but does not engage said movable piston in all open positions of said medical valve.

* * * * *